US012232907B2

(12) United States Patent
Chao et al.

(10) Patent No.: US 12,232,907 B2
(45) Date of Patent: Feb. 25, 2025

(54) INTRALUMINAL ULTRASOUND NAVIGATION GUIDANCE AND ASSOCIATED DEVICES, SYSTEMS, AND METHODS

(71) Applicant: VOLCANO CORPORATION, San Diego, CA (US)

(72) Inventors: Pei-Yin Chao, Eindhoven (NL); Nikhil Sreedhar Rajguru, San Diego, CA (US); Robin Lucia, San Diego, CA (US); Anuja Nair, San Diego, CA (US); Alessandra Di Tullio, Best (NL)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 264 days.

(21) Appl. No.: 16/662,595

(22) Filed: Oct. 24, 2019

(65) Prior Publication Data

US 2020/0129142 A1 Apr. 30, 2020

Related U.S. Application Data

(60) Provisional application No. 62/750,983, filed on Oct. 26, 2018.

(51) Int. Cl.
*A61B 8/08* (2006.01)
*A61B 8/00* (2006.01)
*A61B 8/12* (2006.01)

(52) U.S. Cl.
CPC .............. *A61B 8/0891* (2013.01); *A61B 8/12* (2013.01); *A61B 8/463* (2013.01)

(58) Field of Classification Search
CPC ......... A61B 8/0891; A61B 8/12; A61B 8/463; A61B 8/461; A61B 8/468; A61B 8/5223; A61B 8/465; A61B 8/00
See application file for complete search history.

(56) References Cited

U.S. PATENT DOCUMENTS

| 6,200,268 B1 | 3/2001 | Vince |
| 6,381,350 B1 | 4/2002 | Klingensmith |
| 7,074,188 B2 | 7/2006 | Nair |
| 7,175,597 B2 | 2/2007 | Vince |
| 7,215,802 B2 | 5/2007 | Klingensmith |
| 7,359,554 B2 | 4/2008 | Klingensmith |

(Continued)

FOREIGN PATENT DOCUMENTS

| JP | 2010046229 A | 3/2010 |
| WO | 2019175004 A1 | 9/2019 |

*Primary Examiner* — Sean D Mattson
*Assistant Examiner* — Michael Yiming Fang

(57) ABSTRACT

Disclosed is an intraluminal ultrasound imaging system, comprising a processor circuit in communication with an intraluminal ultrasound imaging catheter, and configured to receive an intraluminal ultrasound image from the imaging catheter within a body lumen of a patient, the body lumen comprising a plurality of segments. The processor is configured to identify a segment of the plurality of segments where the imaging catheter was located when the image was obtained, and output to a display a stylized figure of the body lumen including the plurality of segments, and an indicator identifying the segment in the stylized figure where the imaging catheter was located when the image was obtained.

20 Claims, 18 Drawing Sheets

(56) References Cited

U.S. PATENT DOCUMENTS

| | | | |
|---|---|---|---|
| 7,463,759 B2 | 12/2008 | Klingensmith | |
| 7,846,101 B2 | 12/2010 | Eberle | |
| 7,930,014 B2 | 4/2011 | Huennekens | |
| 8,298,147 B2 | 10/2012 | Huenneken | |
| 2008/0085042 A1* | 4/2008 | Trofimov | G06T 17/00 |
| | | | 600/407 |
| 2009/0163813 A1 | 6/2009 | Ogasawara | |
| 2013/0267848 A1* | 10/2013 | Fearnot | A61B 8/12 |
| | | | 606/200 |
| 2014/0100442 A1 | 4/2014 | Begin | |
| 2014/0187920 A1* | 7/2014 | Millett | A61B 5/7425 |
| | | | 600/424 |
| 2015/0119705 A1* | 4/2015 | Tochterman | A61B 6/504 |
| | | | 600/431 |
| 2016/0074011 A1* | 3/2016 | Johnson | A61F 2/01 |
| | | | 600/424 |
| 2016/0157787 A1* | 6/2016 | Merritt | A61B 5/02007 |
| | | | 600/481 |
| 2016/0157808 A1* | 6/2016 | Merritt | A61B 6/504 |
| | | | 600/407 |
| 2016/0335766 A1* | 11/2016 | Ambwani | G06K 9/4647 |
| 2019/0282199 A1 | 9/2019 | Merritt | |

\* cited by examiner

INTRALUMINAL ULTRASOUND NAVIGATION GUIDANCE AND ASSOCIATED DEVICES, SYSTEMS, AND METHODS

CROSS REFERENCE TO RELATED APPLICATIONS

This application claims priority to and benefit of U.S. Provisional Patent Application No. 62/750,983, filed Oct. 26, 2018, which is incorporated by reference herein in its entirety.

TECHNICAL FIELD

The subject matter described herein relates to a system for medical imaging. In particular, the present disclosure describes aspects related to acquisition, display, identification, and annotation of peripheral intravascular ultrasound or IVUS images, and navigational assistance to the clinician during image acquisition. This system has particular but not exclusive utility for diagnosis and treatment of vascular diseases.

BACKGROUND

Various types of intraluminal imaging systems are used in diagnosing and treating diseases. For example, intravascular ultrasound (IVUS) imaging is used as a diagnostic tool for visualizing vessels within a body of a patient. This may aid in assessing diseased or compressed vessels such as arteries or veins within the human body, determining the need for treatment, optimizing treatment, and/or assessing the effectiveness of a treatment.

Different diseases or medical procedures produce physical features with different size, structure, density, water content, and accessibility for imaging sensors. For example, a deep-vein thrombosis (DVT) produces a clot of blood cells, whereas post-thrombotic syndrome (PTS) produces webbing or other residual structural effects in a vessel that have similar composition to the vessel wall itself, and may thus be difficult to distinguish from the vessel wall. A stent is a dense (e.g., metallic) object that may be placed in a vessel or lumen to hold the vessel or lumen open to a particular diameter. In some cases, intraluminal imaging is carried out with an IVUS device including one or more ultrasound transducers. The IVUS device may be passed into the vessel and guided to the area to be imaged. The transducers emit ultrasonic energy and receive ultrasound echoes reflected from the vessel. The ultrasound echoes are processed to create an image of the vessel of interest. The image of the vessel of interest may include one or more lesions or blockages in the vessel. A stent may be placed within the vessel to treat these blockages and intraluminal imaging may be carried out to view the placement of the stent within the vessel. Other types of treatment include thrombectomy, ablation, angioplasty, pharmaceuticals, etc.

When using IVUS to treat peripheral vascular (PV) disease, it is common that a vascular surgeon handles the IVUS catheter whilst instructing a non-sterile staff member to operate the IVUS console. During a procedure (e.g., a pullback procedure), the vascular surgeon typically instructs the non-sterile operator to bookmark key anatomical landmarks for post IVUS pullback analysis.

Post IVUS pullback analysis may be a tedious effort for the non-sterile (and typically non IVUS expert) staff to label and measure all segments and key frames within segments accurately. However, accurate measurement and labeling is important for auditing, reimbursement, recordkeeping, and optimal treatment planning.

The information included in this Background section of the specification, including any references cited herein and any description or discussion thereof, is included for technical reference purposes only and is not to be regarded as subject matter by which the scope of the disclosure is to be bound.

SUMMARY

Disclosed is a system for computing, displaying, and marking the location of an intravascular imaging probe during an IVUS pullback or other intraluminal procedure that requires accurate knowledge of the location of each IVUS frame within the vasculature. In particular, according to at least one embodiment of the present disclosure, a system is provided for identifying, displaying, and recording the segments of a patient's vasculature associated with live IVUS images captured within the vasculature. This is particularly useful during manually controlled intravascular procedures where detailed knowledge of the imagine probe's location is desired. This system helps make the correlation between IVUS frames and anatomy easier to understand, and provides positional navigation information by visually highlighting the segments in an artery or vessel that need attention. The system can be referred to as an IVUS pullback virtual venogram system. The IVUS pullback virtual venogram system disclosed herein has particular, but not exclusive, utility for intraluminal ultrasound imaging procedures.

The IVUS pullback virtual venogram system includes an intraluminal ultrasound imaging system, including: a processor circuit configured for communication with an intraluminal ultrasound imaging catheter, where the processor circuit is configured to: receive an intraluminal ultrasound image obtained by the intraluminal ultrasound imaging catheter while the intraluminal ultrasound imaging catheter is positioned within a body lumen of a patient, the body lumen including a plurality of segments; identify a segment of the plurality of segments where the intraluminal ultrasound imaging catheter was located when the intraluminal ultrasound image was obtained; and output, to a display in communication with the processor circuit, a screen display including: a stylized figure of the body lumen including the plurality of segments; and an indicator identifying the segment in the stylized figure where the intraluminal ultrasound imaging catheter was located when the intraluminal ultrasound image was obtained.

Implementations may include one or more of the following features. The system where the screen display further includes markers indicating proximal and distal boundaries of one or more of the plurality of segments in the stylized figure. The system where the screen display further includes a marker indicating a location of interest in the stylized figure. The system where the screen display further includes one or more labels respectively identifying one or more segments in the stylized figure. The system where the screen display further includes a position indicator indicating a location within the segment in the stylized figure where the intraluminal ultrasound imaging catheter was located when the intraluminal image was obtained. The system where the processor circuit is configured to sequentially identify the plurality of segments in the stylized figure as the intraluminal ultrasound imaging catheter moves through the plurality of segments. The system where the processor circuit is configured to automatically label the sequentially identified plurality of segments in the stylized figure. The system where the processor circuit is configured to automatically annotate, in the stylized figure, the sequentially identified plurality of segments with a statistically representative reference value associated with a corresponding segment. The system where the processor circuit is configured to automatically annotate, in the stylized figure, the sequentially identified plurality of segments with an automatically measured or calculated value associated with a corresponding segment. The system where the processor circuit is configured to color the sequentially identified plurality of segments based on a ratio of the automatically measured or calculated value to the statistically representative reference value. The system where processor circuit is configured to receive a user input representative of where the intraluminal ultrasound imaging catheter was located when the intraluminal ultrasound image was obtained. The system where the processor circuit is configured to automatically determine, based on the intraluminal ultrasound image, where the intraluminal ultrasound imaging catheter was located when the intraluminal ultrasound image was obtained. The system where the screen display further includes at least one of a longitudinal display of the body lumen, a speed indicator associated with movement of the intraluminal ultrasound imaging catheter, or instructions to a user. The system further including: the intraluminal ultrasound imaging catheter. Implementations of the described techniques may include hardware, a method or process, or computer software on a computer-accessible medium.

One general aspect includes an intraluminal ultrasound imaging method, including: receiving, at a processor circuit in communication with an intraluminal ultrasound imaging catheter, an intraluminal ultrasound image obtained by the intraluminal ultrasound imaging catheter while the intraluminal ultrasound imaging catheter is positioned within a body lumen of a patient, the body lumen including a plurality of segments; and identifying, using the processor circuit, a segment of the plurality of segments where the intraluminal ultrasound imaging catheter was located when the intraluminal ultrasound image was obtained; and outputting, to a display in communication with the processor circuit, a screen display including: a stylized figure of the body lumen including the plurality of segments; and an indicator identifying the segment in the stylized figure where the intraluminal ultrasound imaging catheter was located when the intraluminal ultrasound image was obtained. Other embodiments of this aspect include corresponding computer systems, apparatus, and computer programs recorded on one or more computer storage devices, each configured to perform the actions of the methods.

One general aspect includes an intravascular ultrasound imaging system for use in peripheral vasculature, the system including: an intravascular ultrasound imaging catheter configured to obtain an intravascular ultrasound image while the intravascular ultrasound imaging catheter is positioned within a peripheral blood vessel of a patient, the peripheral blood vessel including a plurality of segments; a processor circuit configured for communication with the intravascular ultrasound imaging catheter, where the processor circuit is configured to: receive the intravascular ultrasound image obtained by the intravascular ultrasound imaging catheter; identify a segment of the plurality of segments where the intravascular ultrasound imaging catheter was located when the intravascular ultrasound image was obtained; and output, to a display in communication with the processor circuit, a screen display including: a stylized figure of the peripheral blood vessel including the plurality of segments; and an indicator identifying the segment in the stylized figure where the intravascular ultrasound imaging catheter was located when the intravascular ultrasound image was obtained. Other embodiments of this aspect include corresponding computer systems, apparatus, and computer programs recorded on one or more computer storage devices, each configured to perform the actions of the methods.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the IVUS pullback virtual venogram system, as defined in the claims, is provided in the following written description of various embodiments of the disclosure and illustrated in the accompanying drawings.

BRIEF DESCRIPTION OF THE DRAWINGS

Illustrative embodiments of the present disclosure will be described with reference to the accompanying drawings, of which.

DETAILED DESCRIPTION

Figure 1:
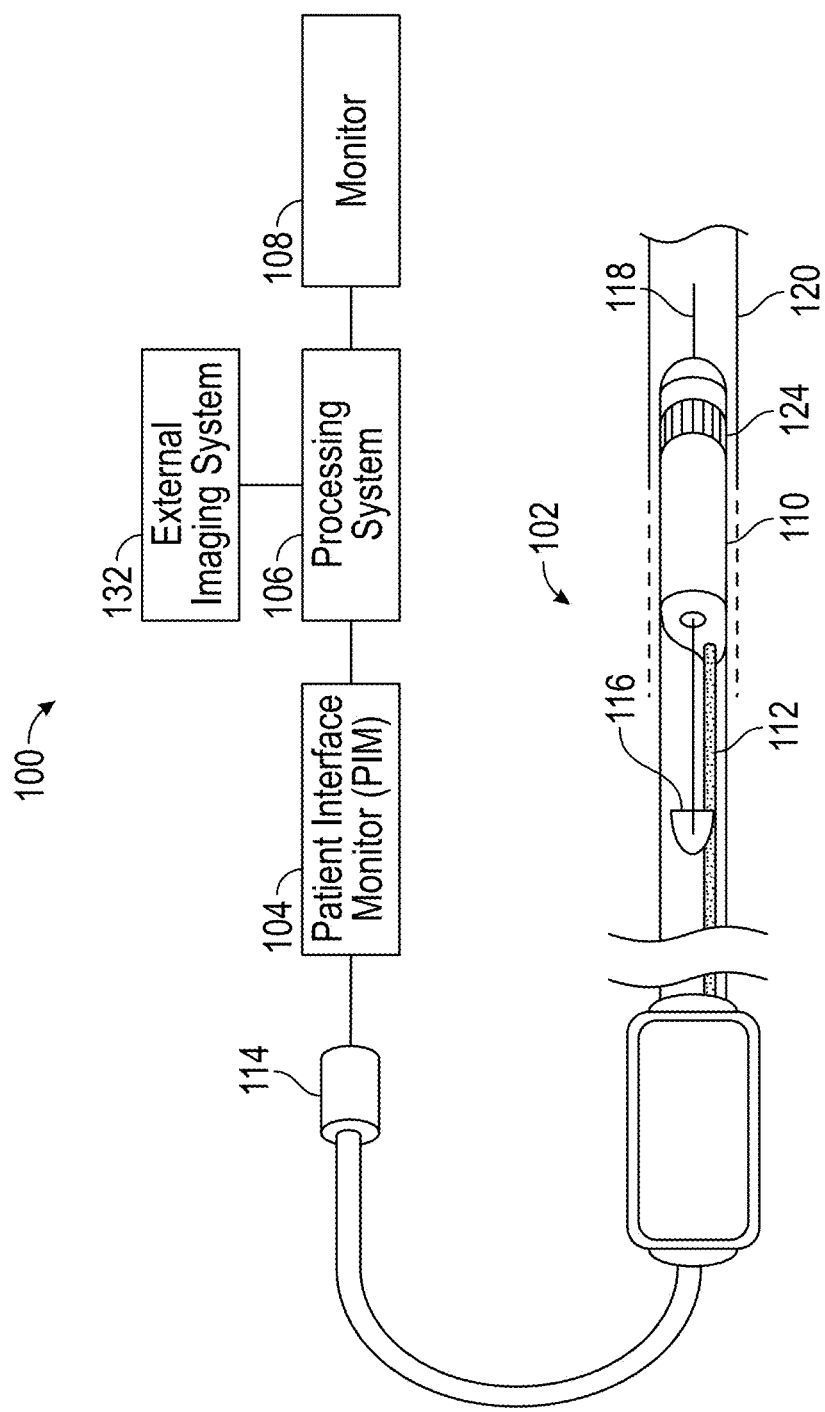
FIG. 1 is a diagrammatic schematic view of an intraluminal imaging system, according to aspects of the present disclosure.

The present disclosure relates generally to medical imaging, including imaging associated with a body lumen of a patient using an intraluminal imaging device. For example, the present disclosure describes systems, devices, and methods for determining and marking the location of an intravascular imaging probe within a patient's vasculature. In accordance with at least one embodiment of the present disclosure, a system is provided for identifying, displaying, and recording the segments of a patient's vasculature associated with live IVUS images captured within the vasculature. This is particularly useful during manually controlled intravascular procedures where detailed knowledge of the imagine probe's location is desired. This system, hereinafter referred to as an IVUS pullback virtual venogram system, helps make the correlation between IVUS frames and anatomy easier to understand, and provides positional navigation information by identifying and visually highlighting the segments in an artery or vessel that need attention.

The devices, systems, and methods described herein can include one or more features described in U.S. Provisional App. No. 62/750,983, filed 26 Oct. 2018, U.S. Provisional App. No. 62/751,268, filed 26 Oct. 2018, U.S. Provisional App. No. 62/751,289, filed 26 Oct. 2018, U.S. Provisional App. No. 62/750,996, filed 26 Oct. 2018, U.S. Provisional App. No. 62/751,167, filed 26 Oct. 2018, and U.S. Provisional App. No. 62/751,185, filed 26 Oct. 2018, each of which is hereby incorporated by reference in its entirety as though fully set forth herein.

The devices, systems, and methods described herein can also include one or more features described in U.S. Provisional App. No. U.S. Ser. No. 62/642,847, filed Mar. 14, 2018 (and a Non-Provisional Application filed therefrom on Mar. 12, 2019 as U.S. Ser. No. 16/351,175), U.S. Provisional App. No. 62/712,009, filed Jul. 30, 2018, U.S. Provisional App. No. 62/711,927, filed Jul. 30, 2018, and U.S. Provisional App. No. 62/643,366, filed Mar. 15, 2018 (and a Non-Provisional Application filed therefrom on Mar. 15, 2019 as U.S. Ser. No. 16/354,970), each of which is hereby incorporated by reference in its entirety as though fully set forth herein.

The present disclosure substantially aids a clinician in orienting, navigating, and guiding an intravascular imaging probe or intraluminal imaging probe within a vessel or lumen of a patient, by providing a venogram-type roadmap during intraluminal medical imaging procedures. The venogram-type roadmap may include stylized, statistically representative human anatomy, along with directionality indicators, automatic measurement tools, step by step navigation or operating instructions, and co-registered vessel maps showing the position of the probe within a patient's anatomy. Implemented on a medical imaging console (e.g., an intraluminal imaging console) in communication with a medical imaging sensor (e.g., an intraluminal ultrasound sensor), the IVUS pullback virtual venogram system disclosed herein provides both time savings and an improvement in the location certainty of captured images. This improved imaging workflow transforms raw imaging data into annotated roadmaps, anatomical measurements, and step-by-step instructions for a clinician to perform a given procedure. This occurs without the normally routine need to manually interpret clinical images to determine their anatomical location and orientation. This unconventional approach improves the functioning of the medical imaging console and sensor, by permitting more efficient workflow and more useful clinical outputs. Aspects of co-registration are described, for example, in U.S. Pat. Nos. 7,930,014 and 8,298,147, the entireties of which are hereby incorporated by reference in its eternity. A stylized figure can include a figure, diagram, drawing, or graphic that is stored in and retrieved from memory (e.g., common for all patients or representative of all patients), or that is generated from data obtained from one or more IVUS images, and is different than an actual image obtained by an imaging device (e.g., x-ray or IVUS).

The IVUS pullback virtual venogram system may be implemented as a set of logical branches and mathematical operations, whose outputs are viewable on a display, and operated by a control process executing on a processor that accepts user inputs from a keyboard, mouse, or touchscreen interface, and that is in communication with one or more medical imaging sensors (e.g., intraluminal ultrasound sensors). In that regard, the control process performs certain specific operations in response to different inputs or selections made by a user at the start of an imaging procedure, and may also respond to inputs made by the user during the procedure. Certain structures, functions, and operations of the processor, display, sensors, and user input systems are known in the art, while others are recited herein to enable novel features or aspects of the present disclosure with particularity.

Various types of intraluminal imaging systems are used in diagnosing and treating diseases. For example, intravascular ultrasound (IVUS) imaging is used as a diagnostic tool for visualizing vessels within a body of a patient. This may aid in assessing diseased or compressed vessels, such as arteries or veins, within the human body to determine the need for treatment, to optimize treatment, and/or to assess a treatment's effectiveness (e.g., through imaging of the vessel before and after treatment).

In some cases, intraluminal imaging is carried out with an IVUS device including one or more ultrasound transducers. The IVUS device may be passed into the vessel and guided to the area to be imaged. The transducers emit ultrasonic energy and receive ultrasound echoes reflected from the vessel. The ultrasound echoes are processed to create an image of the vessel of interest. The image of the vessel of interest may include one or more lesions or blockages in the vessel and/or sites of narrowing by compression. A stent may be placed within the vessel to treat these blockages or narrowings, and intraluminal imaging may be carried out to view the placement of the stent within the vessel. Other types of treatment include thrombectomy, ablation, angioplasty, pharmaceuticals, etc.

Understanding what artery or vessel segment a particular IVUS frame belongs to can be challenging and time consuming, especially because physicians see only the cross-sectional IVUS images and the reconstructed longitudinal view (image longitudinal display or ILD) on the dedicated IVUS screen, without any anatomical reference (bony landmarks) to which they can refer. To understand the position of the IVUS probe with respect to the patient's anatomy, physicians currently look at the fluoroscopy image during pullback, which lies on another screen. Moreover, during peripheral vascular interventions, the anatomical references for the segments' boundaries are confluences and branches with other vessels, which physicians and other users recognize on IVUS while doing pullbacks and on LIVE mode, and that they must mentally memorize. Clinicians may also call out regions of interest to their aides who may be less expert. The IVUS pullback virtual venogram system overcomes the lack of reference landmarks and displays the relative position of an IVUS frame, making IVUS image interpretation easier. The IVUS pullback virtual venogram system depicts this information in one simple, stylized anatomical visualization, which helps image interpretation after completion of a pullback, and provides a contextual visualization of the bookmarked frames. The IVUS pullback virtual venogram system lessens the staff-dependency of vascular surgeons. On completion of the pullback, the IVUS measurement results are automatically plotted on the IVUS pullback virtual venogram system in an easy-to-interpret way.

Marking confluences, healthy frames, and most occluded frames during a pullback is currently typically done by non-sterile staff. In a common scenario, these personnel bookmark on the IVUS screen in response to a physician's command. However, there is often a time delay between the two actions, resulting in a shifted bookmarked frame. In addition, labeling may not be possible while bookmarking, thus making the task of reporting (after the case) more lengthy and cumbersome, as the bookmarks are not differentiated on the ILD view. The IVUS pullback virtual venogram system eases the communication between vascular surgeons and their staff as frames and segments are clearly labelled automatically. The IVUS pullback virtual venogram system saves the non-sterile operator lots of time, make medical records more complete and make case dictation for the vascular surgeon much easier. The IVUS pullback virtual venogram system auto-labels key frames of interest by the vessel segment in which they were captured (e.g. External Iliac Vein (EIV), EIV Ref, EIV Pre Target, etc.).

The IVUS pullback virtual venogram system includes a graphical representation of a venogram, along with positional navigational assistance, vessel and artery segmentation, highlighted segments of interest or attention, IVUS frame location highlight, and automated labelling and prompts.

These descriptions are provided for exemplary purposes only, and should not be considered to limit the scope of the IVUS pullback virtual venogram system. Certain features may be added, removed, or modified without departing from the spirit of the claimed subject matter.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intraluminal imaging system incorporating the IVUS pullback virtual venogram system, according to aspects of the present disclosure. The intraluminal imaging system 100 can be an intravascular ultrasound (IVUS) imaging system in some embodiments. The intraluminal imaging system 100 may include an intraluminal device 102, a patient interface module (PIM) 104, a console or processing system 106, a monitor 108, and an external imaging system 132 which may include angiography, ultrasound, X-ray, computed tomography (CT), magnetic resonance imaging (MRI), or other imaging technologies, equipment, and methods. The intraluminal device 102 is sized and shaped, and/or otherwise structurally arranged to be positioned within a body lumen of a patient. For example, the intraluminal device 102 can be a catheter, guide wire, guide catheter, pressure wire, and/or flow wire in various embodiments. In some circumstances, the system 100 may include additional elements and/or may be implemented without one or more of the elements illustrated in FIG. 1. For example, the system 100 may omit the external imaging system 132.

The intraluminal imaging system 100 (or intravascular imaging system) can be any type of imaging system suitable for use in the lumens or vasculature of a patient. In some embodiments, the intraluminal imaging system 100 is an intraluminal ultrasound (IVUS) imaging system. In other embodiments, the intraluminal imaging system 100 may include systems configured for forward looking intraluminal ultrasound (FL-IVUS) imaging, intraluminal photoacoustic (IVPA) imaging, intracardiac echocardiography (ICE), transesophageal echocardiography (TEE), and/or other suitable imaging modalities.

It is understood that the system 100 and/or device 102 can be configured to obtain any suitable intraluminal imaging data. In some embodiments, the device 102 may include an imaging component of any suitable imaging modality, such as optical imaging, optical coherence tomography (OCT), etc. In some embodiments, the device 102 may include any suitable non-imaging component, including a pressure sensor, a flow sensor, a temperature sensor, an optical fiber, a reflector, a mirror, a prism, an ablation element, a radio frequency (RF) electrode, a conductor, or combinations thereof. Generally, the device 102 can include an imaging element to obtain intraluminal imaging data associated with the lumen 120. The device 102 may be sized and shaped (and/or configured) for insertion into a vessel or lumen 120 of the patient.

The system 100 may be deployed in a catheterization laboratory having a control room. The processing system 106 may be located in the control room. Optionally, the processing system 106 may be located elsewhere, such as in the catheterization laboratory itself. The catheterization laboratory may include a sterile field while its associated control room may or may not be sterile depending on the procedure to be performed and/or on the health care facility. The catheterization laboratory and control room may be used to perform any number of medical imaging procedures such as angiography, fluoroscopy, CT, IVUS, virtual histology (VH), forward looking IVUS (FL-IVUS), intraluminal photoacoustic (IVPA) imaging, a fractional flow reserve (FFR) determination, a coronary flow reserve (CFR) determination, optical coherence tomography (OCT), computed tomography, intracardiac echocardiography (ICE), forward-looking ICE (FLICE), intraluminal palpography, transesophageal ultrasound, fluoroscopy, and other medical imaging modalities, or combinations thereof. In some embodiments, device 102 may be controlled from a remote location such as the control room, such than an operator is not required to be in close proximity to the patient.

The intraluminal device 102, PIM 104, monitor 108, and external imaging system 132 may be communicatively coupled directly or indirectly to the processing system 106. These elements may be communicatively coupled to the medical processing system 106 via a wired connection such as a standard copper link or a fiber optic link and/or via wireless connections using IEEE 802.11 Wi-Fi standards, Ultra Wide-Band (UWB) standards, wireless FireWire, wireless USB, or another high-speed wireless networking standard. The processing system 106 may be communicatively coupled to one or more data networks, e.g., a TCP/IP-based local area network (LAN). In other embodiments, different protocols may be utilized such as Synchronous Optical Networking (SONET). In some cases, the processing system 106 may be communicatively coupled to a wide area network (WAN). The processing system 106 may utilize network connectivity to access various resources. For example, the processing system 106 may communicate with a Digital Imaging and Communications in Medicine (DICOM) system, a Picture Archiving and Communication System (PACS), and/or a Hospital Information System via a network connection.

At a high level, an ultrasound imaging intraluminal device 102 emits ultrasonic energy from a transducer array 124 included in scanner assembly 110 mounted near a distal end of the intraluminal device 102. The ultrasonic energy is reflected by tissue structures in the medium (such as a lumen 120) surrounding the scanner assembly 110, and the ultrasound echo signals are received by the transducer array 124. The scanner assembly 110 generates electrical signal(s) representative of the ultrasound echoes. The scanner assembly 110 can include one or more single ultrasound transducers and/or a transducer array 124 in any suitable configuration, such as a planar array, a curved array, a circumferential array, an annular array, etc. For example, the scanner assembly 110 can be a one-dimensional array or a two-dimensional array in some instances. In some instances, the scanner assembly 110 can be a rotational ultrasound device. The active area of the scanner assembly 110 can include one or more transducer materials and/or one or more segments of ultrasound elements (e.g., one or more rows, one or more columns, and/or one or more orientations) that can be uniformly or independently controlled and activated. The active area of the scanner assembly 110 can be patterned or structured in various basic or complex geometries. The scanner assembly 110 can be disposed in a side-looking orientation (e.g., ultrasonic energy emitted perpendicular and/or orthogonal to the longitudinal axis of the intraluminal device 102) and/or a forward-looking looking orientation (e.g., ultrasonic energy emitted parallel to and/or along the longitudinal axis). In some instances, the scanner assembly 110 is structurally arranged to emit and/or receive ultrasonic energy at an oblique angle relative to the longitudinal axis, in a proximal or distal direction. In some embodiments, ultrasonic energy emission can be electronically steered by selective triggering of one or more transducer elements of the scanner assembly 110.

The ultrasound transducer(s) of the scanner assembly 110 can be a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. In an embodiment the ultrasound transducer array 124 can include any suitable number of individual transducer elements or acoustic elements between 1 acoustic element and 1000 acoustic elements, including values such as 2 acoustic elements, 4 acoustic elements, 36 acoustic elements, 64 acoustic elements, 128 acoustic elements, 500 acoustic elements, 812 acoustic elements, and/or other values both larger and smaller.

The PIM 104 transfers the received echo signals to the processing system 106 where the ultrasound image (including the flow information) is reconstructed and displayed on the monitor 108. The console or processing system 106 can include a processor and a memory. The processing system 106 may be operable to facilitate the features of the intraluminal imaging system 100 described herein. For example, the processor can execute computer readable instructions stored on the non-transitory tangible computer readable medium.

The PIM 104 facilitates communication of signals between the processing system 106 and the scanner assembly 110 included in the intraluminal device 102. This communication may include providing commands to integrated circuit controller chip(s) within the intraluminal device 102, selecting particular element(s) on the transducer array 124 to be used for transmit and receive, providing the transmit trigger signals to the integrated circuit controller chip(s) to activate the transmitter circuitry to generate an electrical pulse to excite the selected transducer array element(s), and/or accepting amplified echo signals received from the selected transducer array element(s) via amplifiers included on the integrated circuit controller chip(s). In some embodiments, the PIM 104 performs preliminary processing of the echo data prior to relaying the data to the processing system 106. In examples of such embodiments, the PIM 104 performs amplification, filtering, and/or aggregating of the data. In an embodiment, the PIM 104 also supplies high- and low-voltage DC power to support operation of the intraluminal device 102 including circuitry within the scanner assembly 110.

The processing system 106 receives echo data from the scanner assembly 110 by way of the PIM 104 and processes the data to reconstruct an image of the tissue structures in the medium surrounding the scanner assembly 110. Generally, the device 102 can be utilized within any suitable anatomy and/or body lumen of the patient. The processing system 106 outputs image data such that an image of the vessel or lumen 120, such as a cross-sectional IVUS image of the lumen 120, is displayed on the monitor 108. Lumen 120 may represent fluid filled or fluid-surrounded structures, both natural and man-made. Lumen 120 may be within a body of a patient. Lumen 120 may be a blood vessel, such as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

The controller or processing system 106 may include a processing circuit having one or more processors in communication with memory and/or other suitable tangible computer readable storage media. The controller or processing system 106 may be configured to carry out one or more aspects of the present disclosure. In some embodiments, the processing system 106 and the monitor 108 are separate components. In other embodiments, the processing system 106 and the monitor 108 are integrated in a single component. For example, the system 100 can include a touch screen device, including a housing having a touch screen display and a processor. The system 100 can include any suitable input device, such as a touch sensitive pad or touch screen display, keyboard/mouse, joystick, button, etc., for a user to select options shown on the monitor 108. The processing system 106, the monitor 108, the input device, and/or combinations thereof can be referenced as a controller of the system 100. The controller can be in communication with the device 102, the PIM 104, the processing system 106, the monitor 108, the input device, and/or other components of the system 100.

In some embodiments, the intraluminal device 102 includes some features similar to traditional solid-state IVUS catheters, such as the EagleEye® catheter available from Philips and those disclosed in U.S. Pat. No. 7,846,101 hereby incorporated by reference in its entirety. For example, the intraluminal device 102 may include the scanner assembly 110 near a distal end of the intraluminal device 102 and a transmission line bundle 112 extending along the longitudinal body of the intraluminal device 102. The cable or transmission line bundle 112 can include a single conductor or a plurality of conductors, including two, three, four, five, six, seven, or more conductors.

The transmission line bundle 112 terminates in a PIM connector 114 at a proximal end of the intraluminal device 102. The PIM connector 114 electrically couples the transmission line bundle 112 to the PIM 104 and physically couples the intraluminal device 102 to the PIM 104. In an embodiment, the intraluminal device 102 further includes a guidewire exit port 116. Accordingly, in some instances the intraluminal device 102 is a rapid-exchange catheter. The guidewire exit port 116 allows a guidewire 118 to be inserted towards the distal end in order to direct the intraluminal device 102 through the lumen 120.

The monitor 108 may be a display device such as a computer monitor or other type of screen. The monitor 108 may be used to display selectable prompts, instructions, and visualizations of imaging data to a user. In some embodiments, the monitor 108 may be used to provide a procedure-specific workflow to a user to complete an intraluminal imaging procedure. This workflow may include performing a pre-stent plan to determine the state of a lumen and potential for a stent, as well as a post-stent inspection to determine the status of a stent that has been positioned in a lumen. The workflow may be presented to a user as any of the displays or visualizations shown in FIGS. 5-7.

The external imaging system 132 can be configured to obtain x-ray, radiographic, angiographic/venographic (e.g., with contrast), and/or fluoroscopic (e.g., without contrast) images of the body of a patient (including the vessel 120). External imaging system 132 may also be configured to obtain computed tomography images of the body of patient (including the vessel 120). The external imaging system 132 may include an external ultrasound probe configured to obtain ultrasound images of the body of the patient (including the vessel 120) while positioned outside the body. In some embodiments, the system 100 includes other imaging modality systems (e.g., MRI) to obtain images of the body of the patient (including the vessel 120). The processing system 106 can utilize the images of the body of the patient in conjunction with the intraluminal images obtained by the intraluminal device 102.

Figure 2:
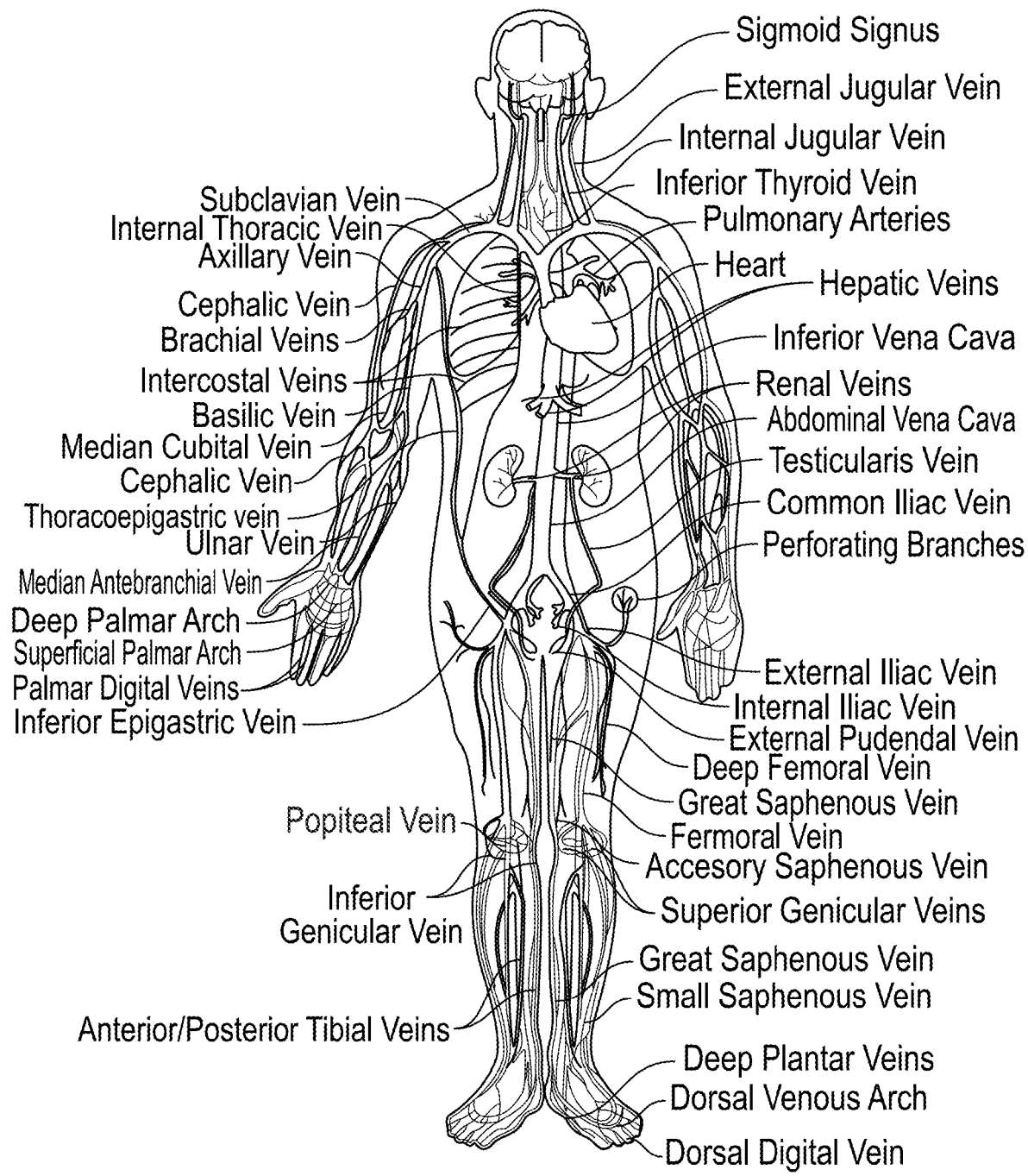
FIG. 2 illustrates blood vessels (e.g., arteries and veins) in the human body.

FIG. 2 illustrates blood vessels (e.g., arteries and veins) in the human body. For example, veins of the human body are labeled. Aspects of the present disclosure can be related to peripheral vasculature, e.g., veins in the torso or legs.

Occlusions can occur in arteries or veins. An occlusion can be generally representative of any blockage or other structural arrangement that results in a restriction to the flow of fluid through the lumen (e.g., an artery or a vein), for example, in a manner that is deleterious to the health of the patient. For example, the occlusion narrows the lumen such that the cross-sectional area of the lumen and/or the available space for fluid to flow through the lumen is decreased. Where the anatomy is a blood vessel, the occlusion may be a result of narrowing due to compression (e.g., from external vessels) plaque buildup, including without limitation plaque components such as fibrous, fibro-lipidic (fibro fatty), necrotic core, calcified (dense calcium), blood, and/or different stages of thrombus (acute, sub-acute, chronic, etc.). In some instances, the occlusion can be referenced as thrombus, a stenosis, and/or a lesion. Generally, the composition of the occlusion will depend on the type of anatomy being evaluated. Healthier portions of the anatomy may have a uniform or symmetrical profile (e.g., a cylindrical profile with a circular cross-sectional profile). The occlusion may not have a uniform or symmetrical profile. Accordingly, diseased or compressed portions of the anatomy, with the occlusion, will have a non-symmetric and/or otherwise irregular profile. The anatomy can have one occlusion or multiple occlusions.

Build-up of an occlusion (e.g., thrombus, deep vein thrombosis or DVT, chronic total occlusion or CTO, etc.) is one way in which the cross-sectional area of the vein in the peripheral vasculature (e.g., torso, abdomen, groin, leg) may be reduced. Other anatomy that contacts the vein can also reduce its cross-sectional area, thereby restricting blood flow therethrough. For example, arteries or ligaments in the torso, abdomen, groin, or leg can press against a vein, which changes the shape of the vein and reduces its cross-sectional area. Such reductions in cross-sectional area resulting from contact with other anatomy can be referenced as compression, in that the walls of the vein are compressed as a result of the contact with the artery or ligament.

Figure 3:
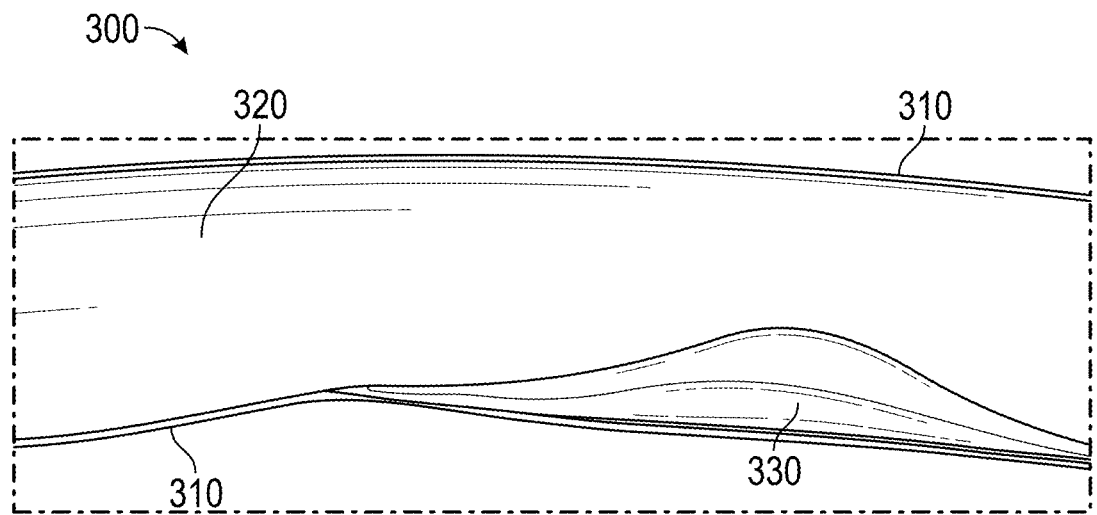
FIG. 3 illustrates a blood vessel incorporating a thrombus.

FIG. 3 illustrates a blood vessel 300 incorporating a thrombus 330. The thrombus occurs between the vessel walls 310 and may restrict the flow of blood 320. Thrombuses come in many types, including sub-acute thrombus, acute thrombus, and chronic thrombus.

Figure 4:
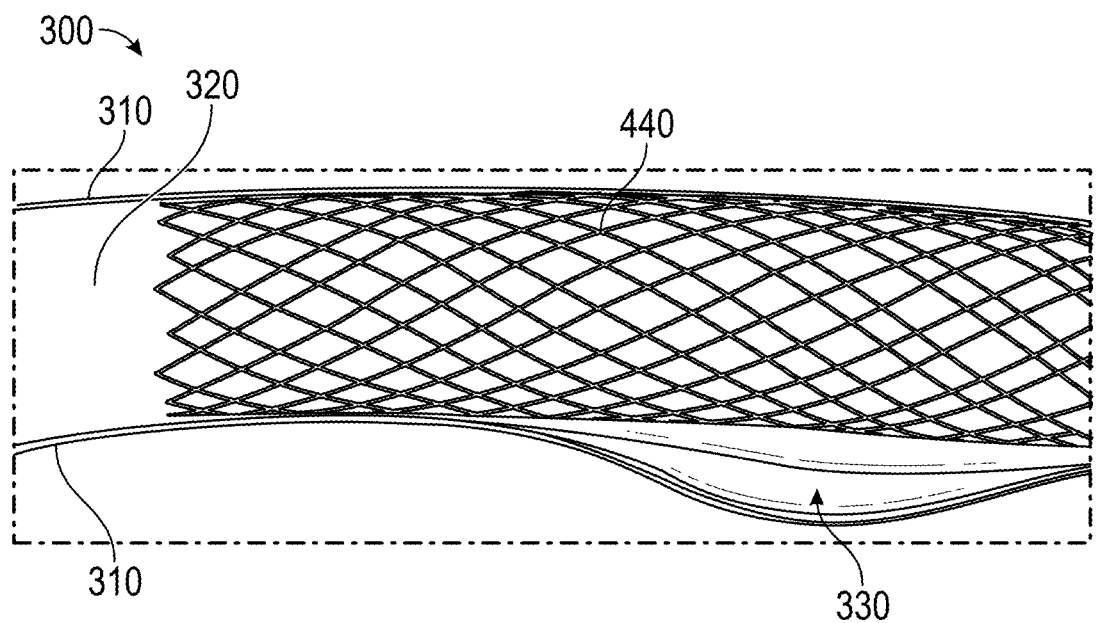
FIG. 4 illustrates a blood vessel incorporating a thrombus and with a stent expanded within it to restore flow.

FIG. 4 illustrates a blood vessel 300 incorporating a thrombus 330 and with a stent 440 expanded within it to restore flow. The stent 440 compresses and arrests the thrombus 330, opening the blood vessel 300 and preventing the thrombus 330 from traveling through the blood vessel 300. The stent 440 also pushes the vessel walls 310 outward, thus reducing the flow restriction for the blood 320. Other treatment options for alleviating an occlusion may include but are not limited to thrombectomy, ablation, angioplasty, and pharmaceuticals. However, in a large majority of cases it may be highly desirable to obtain accurate and timely intravascular images of the affected area, along with accurate and detailed knowledge of the location of the affected area prior to, during, or after treatment. Inaccurate or imprecise location information for IVUS images may, for example, carry a risk of ablation or stenting of healthy tissue instead of diseased or compressed tissue during treatment.

FIGS. 5-23 illustrate exemplary screen displays or graphical user interfaces (GUIs). The screen displays can be generated in a processor 106 and shown (e.g., displayed) on a display or monitor 108 of the system 100, for example, a display of a console, a cart, a bedside controller, a mobile device (e.g., smartphone, tablet, personal digital assistant or PDA), a laptop computer, a desktop computer, etc. The display 108 can be touchscreen display. The display 108 can be in communication with a computer or processing system 106 with a processing circuit (e.g., one or more processors and memory). The processing circuit can generate and output the display data to cause the display 108 to show the screen displays of FIGS. 5-23. The computer, processing circuit, and/or processor 106 can also be in communication with a user interface on which user provides inputs. The inputs can be selections of items on the screen displays. The user interface can be a touchscreen display in some instances. The user interface can be a keyboard, a mouse, a controller with buttons, joystick, etc.

FIGS. 5-9 illustrate screen displays providing the guidance to the clinician during a IVUS pullback in peripheral vasculature. The screen displays advantageously provide a user with additional clarity to more clearly visualize aspects of deep venous disease. The screen displays perform several functions, including highlighting the segments of the vasculature, labeling the segments, and color coding or otherwise highlighting/distinguishing the segments and/or neighboring anatomy. The screen displays also automatically provide reference and compression measures (e.g., cross-sectional lumen area, diameter, etc.) within each of the segments. Segments meeting certain criteria (e.g., greater than or equal to 50% difference between reference and compression measures) are colored, highlighted, bolded, or marked differently (e.g., colored red) to indicate a segment of clinical interest or concern. Additionally, the screen displays provide real time feedback for the user about pullback speed. The GUIs can also provide for image quality improvement by provided the ability to adjust contrast, gain, focus, and/or other image settings. Image quality can also be improved based on providing feedback to the user to reach the correct pullback speed to obtain sufficient amount of high quality IVUS data. The screen displays provide: map to anatomy directly, immediate live values (reference, compression measurements), color coded segment highlights, pullback speed gauge (guidance).

As shown, the screen displays of FIGS. 5-9 include a graphical representation of the peripheral vasculature (e.g., inferior vena cava, abdominal vena cava, renal veins, left and right common iliac veins, left and right common femoral veins, etc.) in which the intraluminal ultrasound device (e.g., IVUS catheter) is positioned. The graphical representations can be an illustration or cartoon of the vasculature (e.g., a virtual or non-medical image venogram) and/or an x-ray/CT/MRI image. For example, the graphical representation can be a roadmap image. The graphical representations can be formed from the obtained IVUS images. The graphical representations illustrate the longitudinal extent of the vasculature and can be referenced as a longitudinal display or image longitudinal display (ILD).

Figure 5:
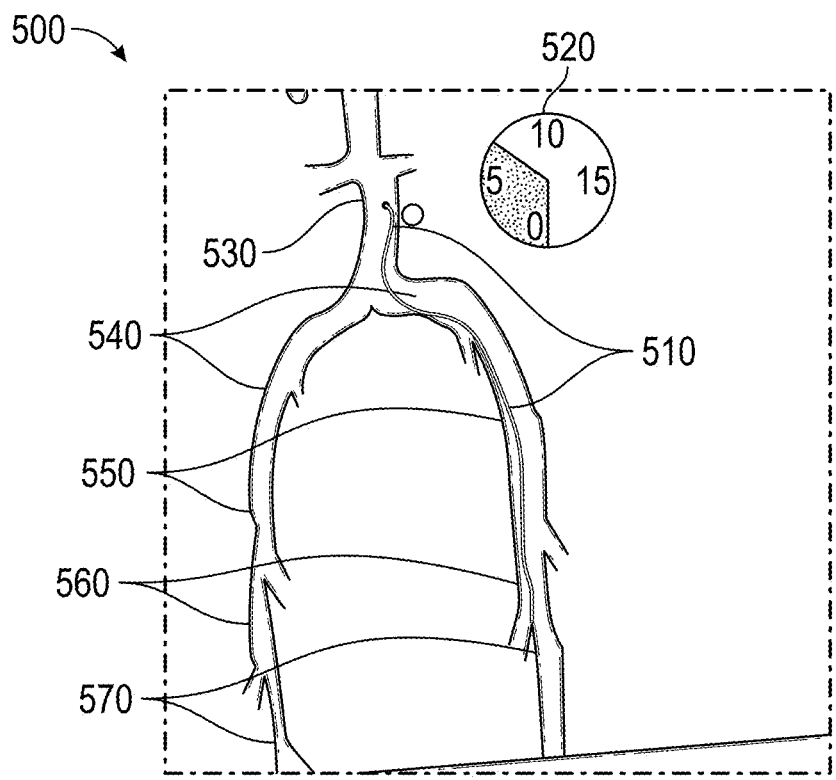
FIG. 5 shows a screen display of an exemplary cartoon roadmap or virtual venogram at the start of a pullback procedure of an imaging catheter in the inferior vena cava or abdominal vena cava in accordance with at least one embodiment of the present disclosure.

A graphical representation of the IVUS catheter, including the flexible elongate member positioned within the vasculature and the transducer array at the distal portion of the flexible elongate member, is also displayed in some embodiments. The position of the IVUS catheter within the vasculature changes from FIGS. 5-9 during the imaging pullback. As shown in FIG. 5, the IVUS catheter starts with transducer array positioned within the inferior or abdominal vena cava. During the pullback, the transducer array moves longitudinally within the vasculature, through the left iliac vein (e.g., FIG. 7), to the left femoral vein (e.g., FIG. 9).

In some embodiments, the user needs to mark key anatomical landmarks such as CIV, EIV and CFV as the imaging catheter passes through or by them during a pullback recording. In other embodiments, the system can automatically detect these landmarks based on image analysis. In some embodiments, the accuracy of the automated analysis is further enhanced by introducing a step where the user indicates the point of entry (femoral, jugular, left leg/right leg) to the system before commencing the pullback. In some embodiments, the system can also detect and highlight neighboring areas of interest as the imaging proceeds.

FIG. 5 shows a screen display of an exemplary cartoon roadmap or virtual venogram 500 at the start of a pullback procedure of an imaging catheter 510 in the inferior vena cava or abdominal vena cava 530 in accordance with at least one embodiment of the present disclosure. A speed indicator 520 is provided to provide guidance about the pullback speed. The pullback speed affects the amount of imaging data collected at locations along the length of the vasculature, and therefore the image quality of the IVUS images at those locations. Different colors, shadings, text, numerical values, etc. within the speed indicator 520 can alert the user about whether to speed up (go faster), slow down (go slower), and/or maintain speed during the pullback. For example, a speed gauge with numerical values is shown in FIGS. 5-9. All or a portion of the speed gauge can be colored to guide the user. For example, in FIGS. 5, 6, and 7, a colored (e.g., green) highlight on the speed gauge indicates that the user is pullback speed is appropriate and should be maintained.

Also visible in this example are the left and right common iliac vein (CIV) 540 left and right external iliac vein (EIV) 550, left and right common femoral veins (CFV) 560, and left and right femoral veins (F) 570. In other examples, other vasculature may be visualized instead or in addition to that shown in FIG. 5.

Figure 6:
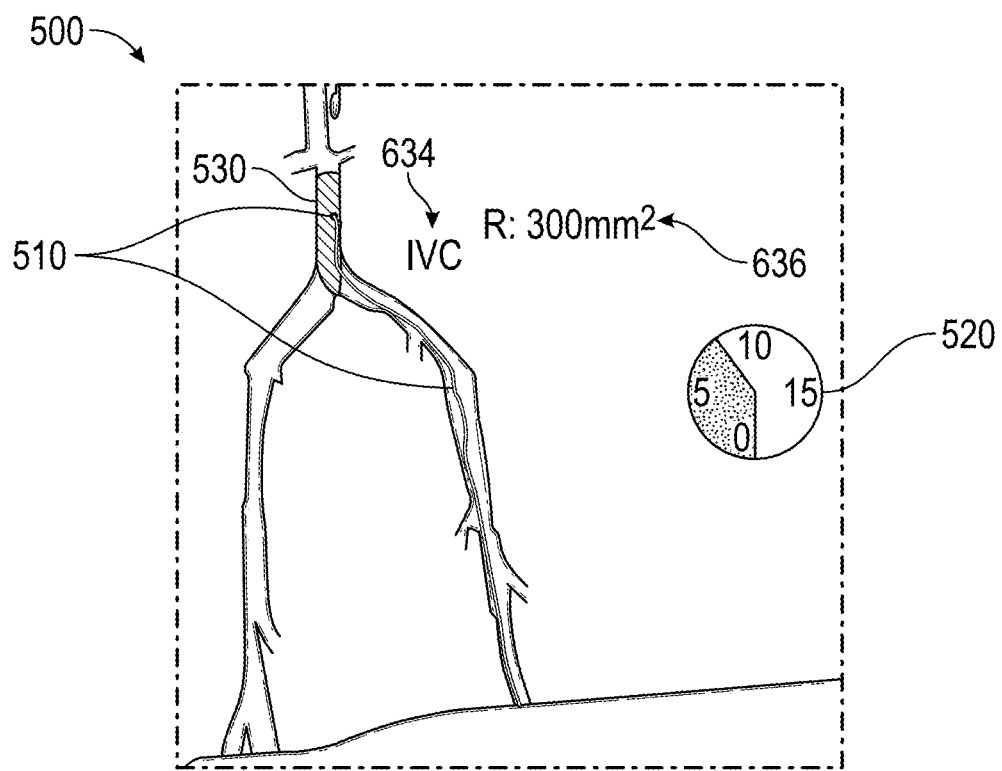
FIG. 6 shows a screen display of an exemplary cartoon roadmap or virtual venogram during a pullback procedure of an imaging catheter in the inferior vena cava, in accordance with at least one embodiment of the present disclosure.

FIG. 6 shows a screen display of an exemplary cartoon roadmap or virtual venogram 500 during a pullback procedure of an imaging catheter 510 in the inferior vena cava, in accordance with at least one embodiment of the present disclosure. In this example, the virtual venogram 500 now includes a text label 634 ("IVC") adjacent to the vasculature to identify the inferior vena cava 530 as the segment of the vasculature currently occupied by the catheter 510, corresponding to the highlighted segment of the virtual venogram 500. For example, the label can be an abbreviation or the full form of the name of the corresponding vasculature segment.

The screen display also automatically provides a statistically representative reference value 636 associated with the vasculature segment 530, adjacent to the vasculature segment 530. The reference value may be an expected value for a healthy vessel, based on literature, for example. The reference value may be the value for a healthy vessel for the particular patient. For example, the reference value may be a numerical value of the cross-sectional lumen area. The numerical value shown in FIG. 6 is exemplary only and does not necessarily reflect the values associated with the specific anatomy. In this example, the inferior vena cava or abdominal vena cava 530 has been colored, shaded, and/or highlighted in the virtual venogram 500, such as in a first color (e.g., blue). The color for the IVC segment can be different than colors associated with other vasculature segments to indicate that it is the start of the pullback. The color of the segment can also indicate that no compression measure is determined from the obtained IVUS data or that the compression measure is equal or approximately equal to the reference measure.

Figure 7:
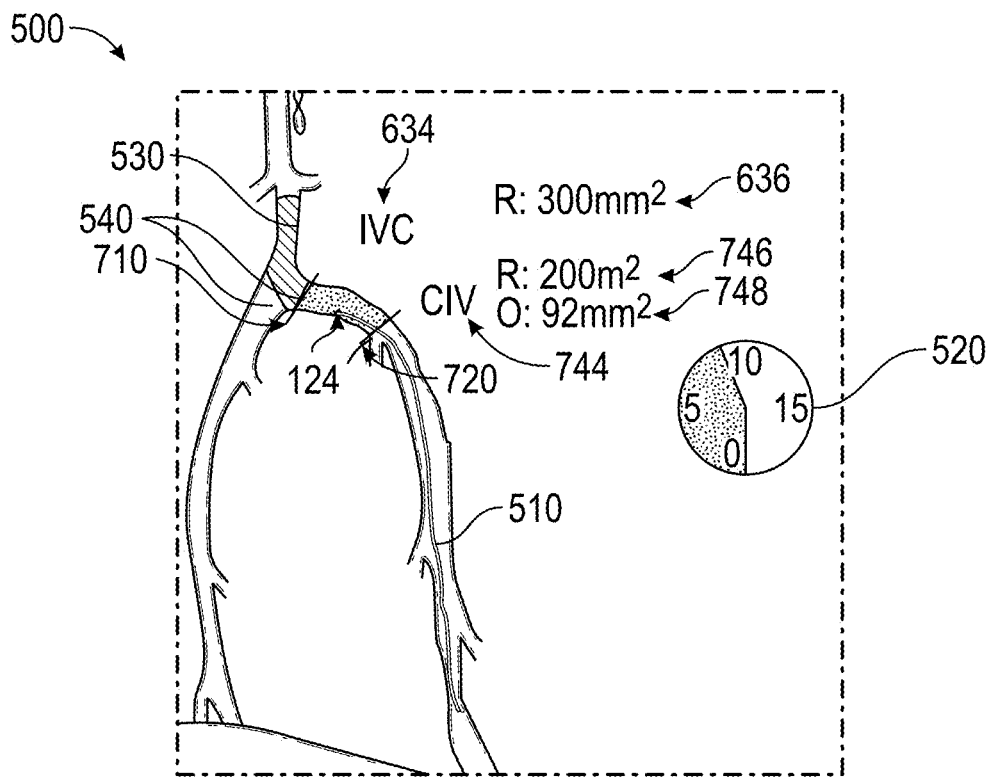
FIG. 7 illustrates the screen display of an exemplary virtual venogram after the transducer array at the end of the catheter has been moved into the left common iliac vein, in accordance with at least one embodiment of the present disclosure.

FIG. 7 illustrates the screen display of an exemplary virtual venogram 500 after the transducer array 124 at the end of the catheter 510 has been moved into the left common iliac vein 540, in accordance with at least one embodiment of the present disclosure. A text label 744 ("CIV") is provided adjacent to the vasculature to identify the segment occupied by the transducer array as the left common iliac vein 540. If the catheter were in the patient's right leg rather than the left leg as in this example, then the CIV 540 on the left half of the virtual venogram 500 would be labeled, and the CIV 540 on the right half of the virtual venogram 500 would be blank.

In this example, a reference value 746 and compression value 748 associated with the CIV segment 540 are automatically provided on the screen display as the transducer array 124 moves within the vasculature. For example, the compression value 748 may be a numerical value of the cross-sectional lumen area for the particular patient, or a % compression value. In that regard, the compression value is automatically calculated based on the obtained IVUS data and then output to the screen display adjacent to the virtual venogram 500. In this example, the CIV segment 540 is colored based on the comparison between the reference value and the compression value. For example, comparison can be a ratio of the compression value 748 and the reference value 746 (e.g., compression value divided by reference value). In this example, the CIV segment 540 is colored differently than the IVC segment 540. For example, when the compression value 748 is less than 50% of the reference value 746, the segment can be colored in a second color (e.g., green) to indicate that the amount of compression is potentially harmful to the patient. Different colorings, shadings, highlighting can be used for the comparison of the reference value 746 and compression value 748 (e.g., different colors for greater than 50%, less than 50%, between 0% and 25%, between 25 and 50%, between 50% and 75%, between 75% and 100%).

Also visible are two position indicators 710 and 720, marking the boundaries of the CIV segment 540. As the pullback continues and the catheter 510 is withdrawn downward (i.e., distally or toward the patient's foot in this example) through the vasculature, the transducer array 124 will eventually cross position indicator 720, and the transducer array 124 will no longer be in the CIV segment 540.

Figure 8:
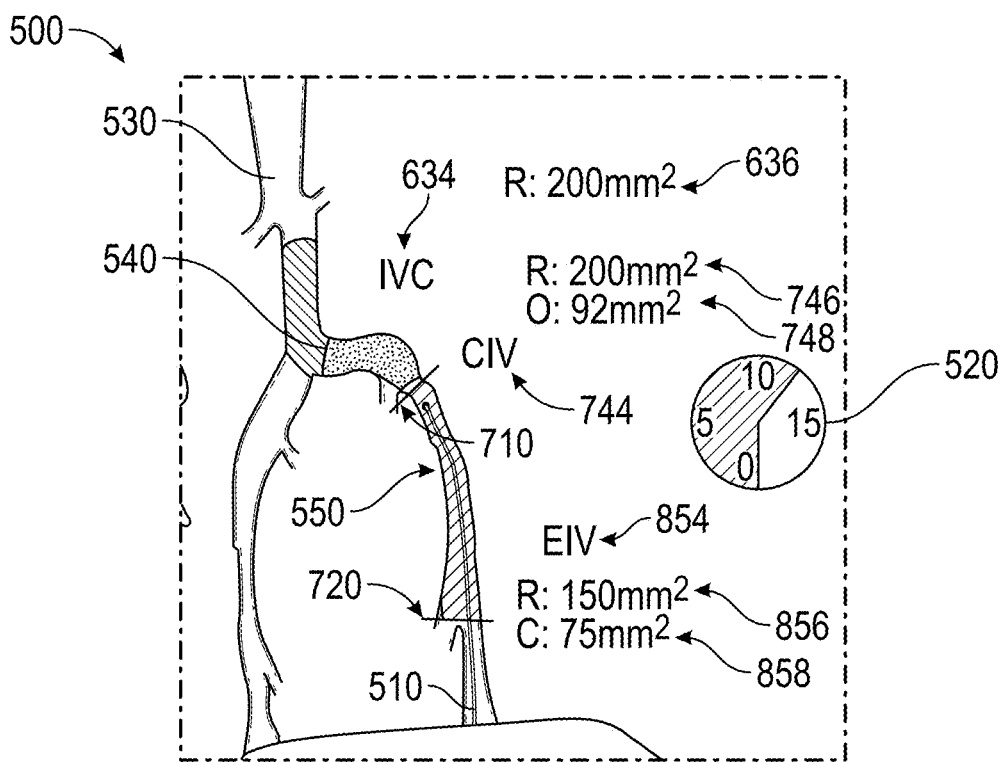
FIG. 8 illustrates the screen display of an exemplary cartoon roadmap or virtual venogram after the transducer array at the end of the catheter has been moved into the left external iliac vein, in accordance with at least one embodiment of the present disclosure.

FIG. 8 illustrates the screen display of an exemplary cartoon roadmap or virtual venogram 500 after the transducer array 124 at the end of the catheter 510 has been moved into the left external iliac vein 550, in accordance with at least one embodiment of the present disclosure. A text label 854 ("EIV") is provided adjacent to the vasculature to identify the segment occupied by the transducer array 124 as the external iliac vein. The reference value 856 and compression value 858 associated with the EIV segment are automatically provided and/or calculated. The EIV segment 550 is colored differently than the IVC and CIV segments 530 and 540, based on the comparison between the reference value 856 and the compression value 858. For example, when the compression value is equal to or greater than 50% of the reference value, the EIV segment can be colored in a third color (e.g., red) to indicate that the amount of compression is potentially harmful to the patient.

FIG. 8 also illustrates the speed gauge 520 indicating that the pullback speed is too high. In that regard, a greater proportion of the speed gauge is colored (compared to e.g., FIGS. 5-7) to show a higher pullback speed. In this example, the speed gauge 520 is colored (e.g., red) to provide real time feedback to the user that the pullback speed should be slowed. Also visible are the position markers 710 and 720, now marking the proximal and distal boundaries of the EIV segment 550.

Figure 9:
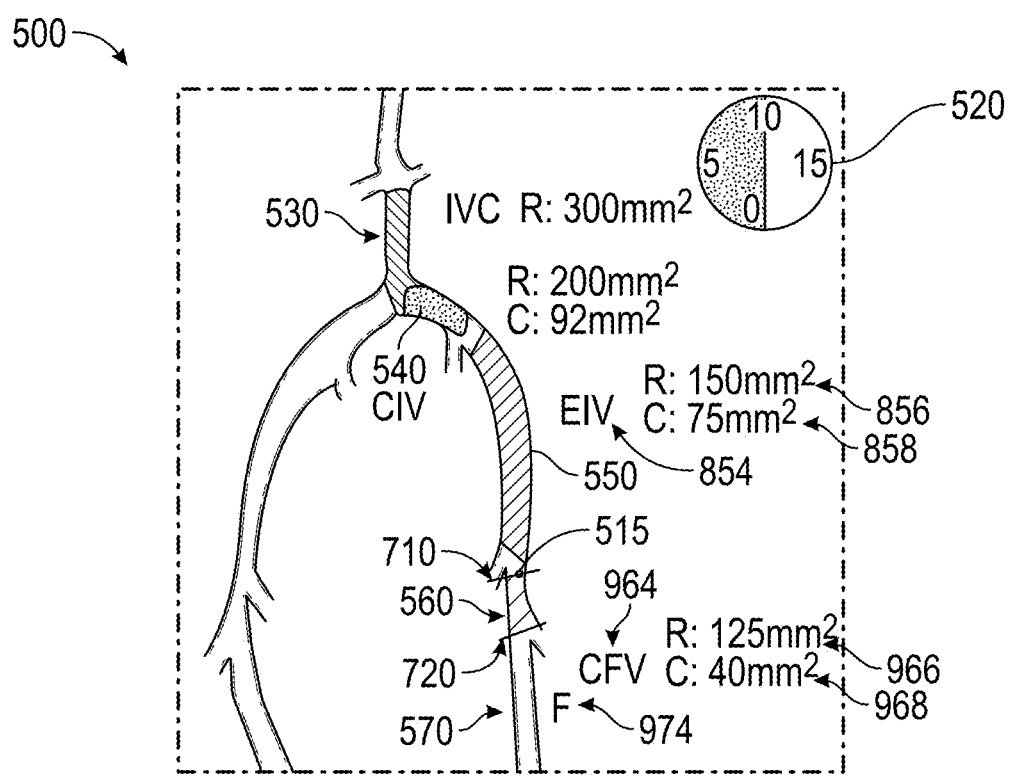
FIG. 9 illustrates the screen display of an exemplary virtual venogram after the transducer array at the end of the catheter has been moved into the left common femoral vein, in accordance with at least one embodiment of the present disclosure.

FIG. 9 illustrates the screen display of an exemplary virtual venogram 500 after the transducer array 124 at the end of the catheter 510 has been moved into the left common femoral vein 560, in accordance with at least one embodiment of the present disclosure. The vasculature segments have been sequentially highlighted ion the virtual venogram 500 as the transducer array passes through them. A text label 964 ("CFV") is provided adjacent to the vasculature to identify the segment occupied by the transducer array 124 of the catheter 510 as the common femoral vein 560. The reference value 966 and compression value 968 associated with the CFV segment 560 are automatically provided and/or calculated. The CFV segment 560 is colored differently than the IVC, CIV, and EIV segments, based on the comparison between the reference value and the compression value. For example, when the compression value is greater than 50% of the reference value, the segment 560 can be colored in a fourth color (e.g., yellow) to indicate that the amount of compression or blockage is not harmful to the patient.

Also visible are the position indicators 710 and 720, now marking the proximal and distal boundaries of the right CFV segment 560. In this example, the left femoral vein 570 also has a label ("F") 974, although no reference value, compression value, or color are displayed, as the transducer array 515 has not yet been pulled back into the right F segment 570.

Figure 10:
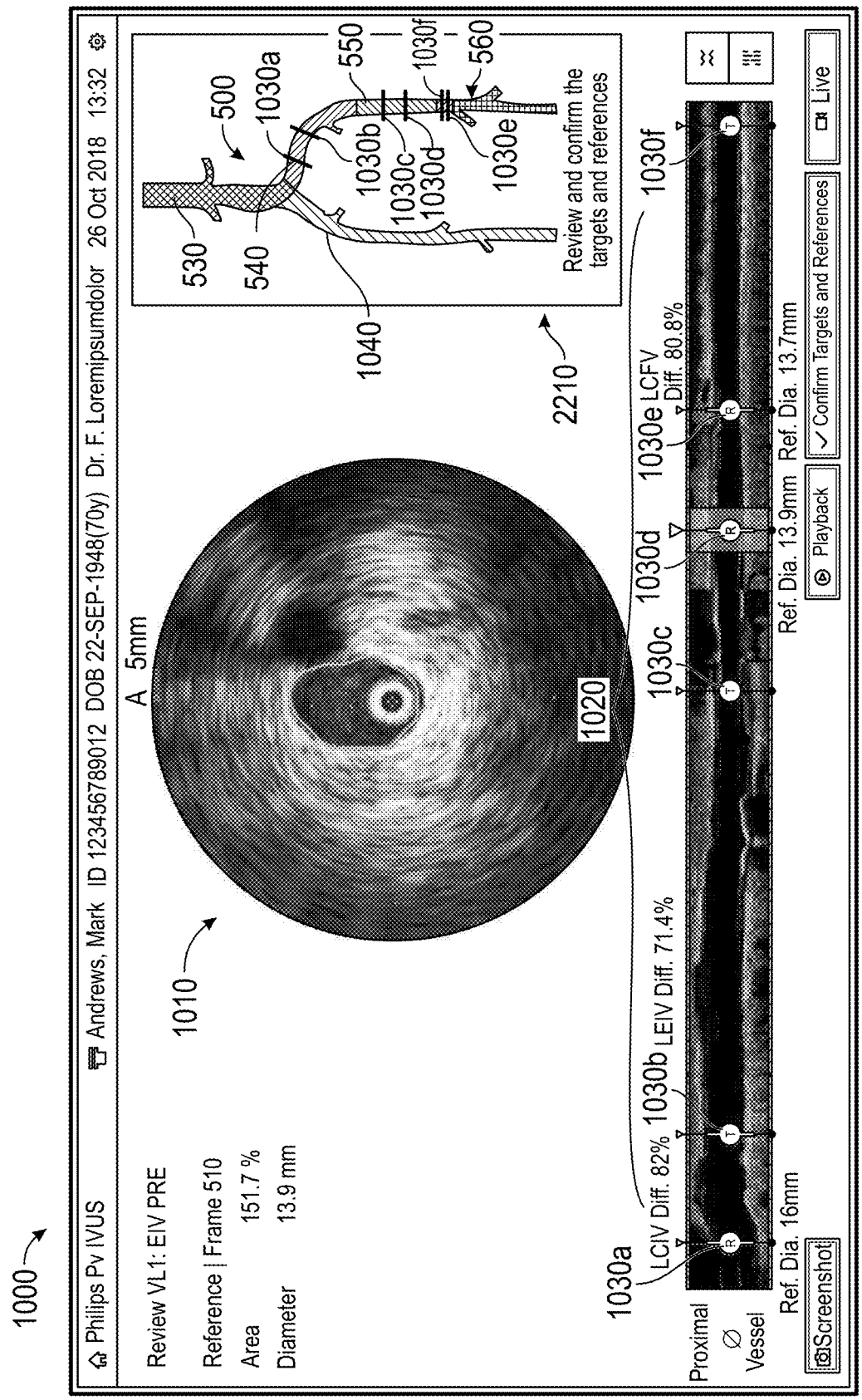
FIG. 10 is a screenshot of an example IVUS system incorporating a virtual venogram in accordance with at least one embodiment of the present disclosure.

FIG. 10 is a screenshot 1000 of an example IVUS system incorporating a virtual venogram 500 in accordance with at least one embodiment of the present disclosure. The screenshot 1000 also includes a tomographic IVUS image 1010 and IVUS image longitudinal display (ILD) 1020. In this example, the left side 1040 of the virtual venogram 500 is displayed in a very faint color (e.g., dark gray against a black background), to indicate that the left side of the body is not under examination. The inferior vena cava 530, common iliac vein 540, and common femoral vein 560 are displayed in a more visible color (e.g., a lighter gray), to show they are along the path of the current pullback procedure, and the external iliac vein 550 is highlighted in a color (e.g., blue) for emphasis (e.g., because this is the segment that contains a thrombus, compression, or other restriction).

Position markers 1030 are displayed within both the virtual venogram 500 and the ILD 1020, marking locations of interest where (for example) IVUS images may be bookmarked for later review. Position markers 1030a and 1030b are located in the right common iliac vein 540, whereas position markers 1030c and 1030d are located in the right external iliac vein 550, and position markers 1030e and 1030f are located in the right common femoral vein 560.

Figure 11A:
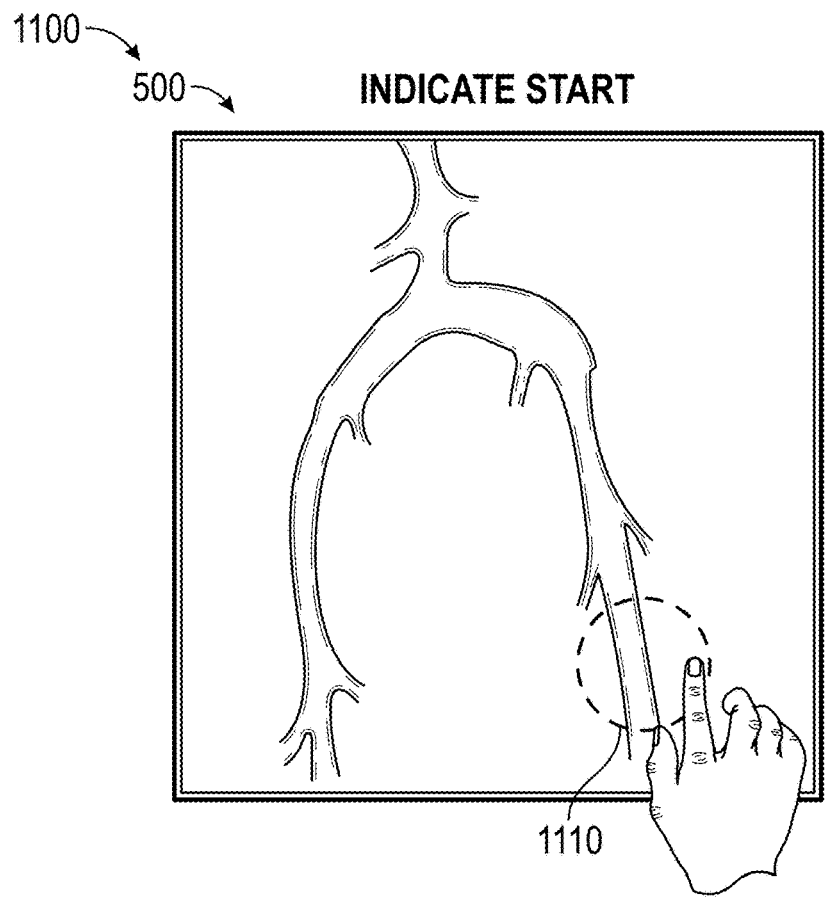
FIG. 11A illustrates a screen display of a virtual venogram at the start of a pullback procedure, in accordance with at least one embodiment of the present disclosure.
Figure 11B:
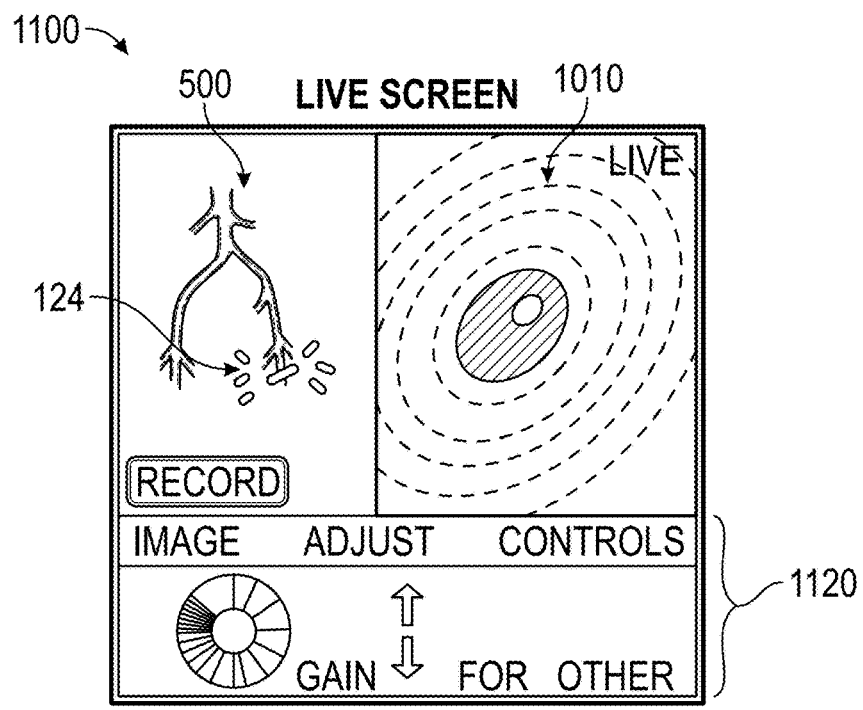
FIG. 11B illustrates screen display of a live view during a pullback procedure in accordance with at least one embodiment of the present disclosure.
Figure 12:
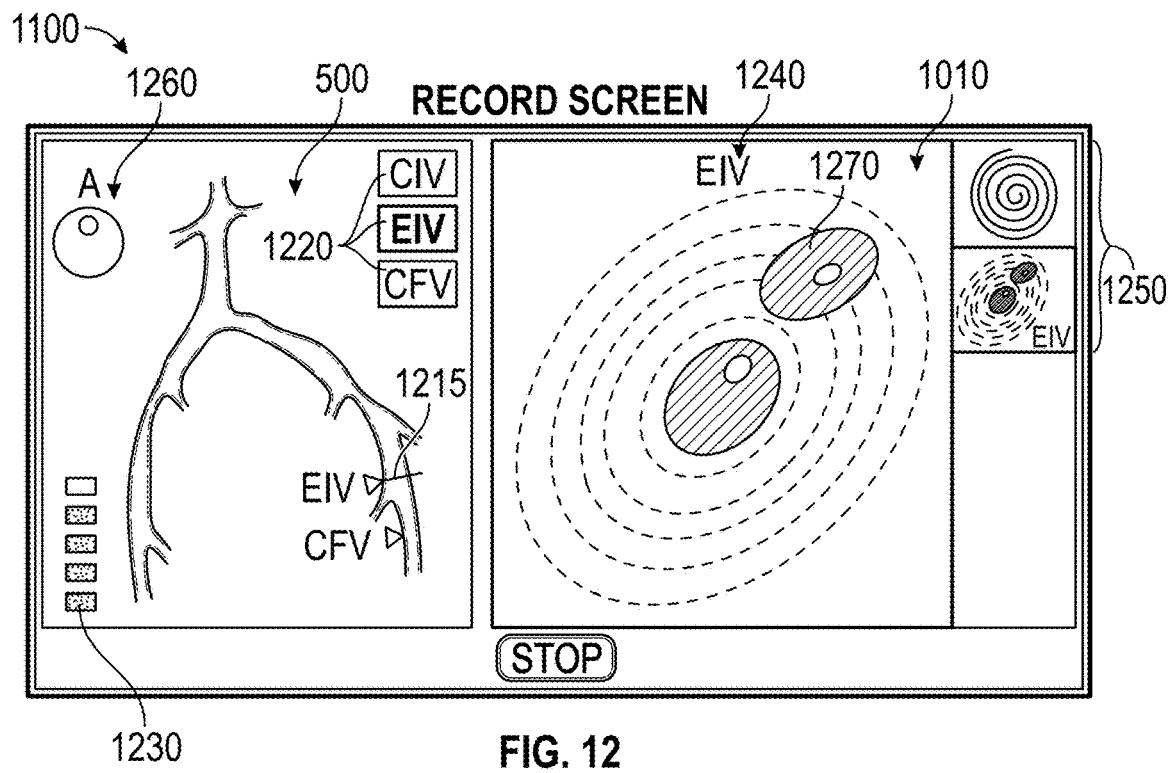
FIG. 12 illustrates a screen display during pullback, e.g., during recording of the IVUS data, in accordance with at least one embodiment of the present disclosure.

FIGS. 11-12 illustrates screen displays providing the user guidance during and after a IVUS pullback in peripheral vasculature. The screen displays provide: auto-label based on anatomical landmark information (e.g., arterial branching), auto-label based on image analysis, bookmark thumbnails on the side, roadmap view (e.g., virtual venogram or actual venogram, the latter of which may be co-registered with tomographic image data), segment mapping, longitudinal and compression indicator, auto-label on all relevant parts, user selected access point, image adjustment, and pullback speed indicator.

FIG. 11A illustrates a screen display 1100 of a virtual venogram at the start of a pullback procedure, in accordance with at least one embodiment of the present disclosure. As shown by a start indicator 1110, the user indicates where on anatomy he or she is starting the pullback on the graphical view of vasculature displayed in the virtual venogram 500. This information serves as an input to the IVUS pullback virtual venogram system, to aid in automatically identifying the different vein segments 530, 540, 550, 560, and 570 as the IVUS transducer array 124 passes through them.

FIG. 11B illustrates screen display 1100 of a live view during a pullback procedure in accordance with at least one embodiment of the present disclosure. A virtual venogram 500, acting as a roadmap in the live view 1100, automatically shows where the transducer array 124 is located within the body. In some embodiments, a co-registered X-ray, CAT scan, or fluoroscopy image may be used as a roadmap instead of or in addition to the virtual venogram 500. The screen display 1100 also includes a live tomographic IVUS image 1010. In addition, the screen display 1100 includes image setting controls 1120 (e.g., gain, field of view, etc.).

FIG. 12 illustrates a screen display 1100 during pullback, e.g., during recording of the IVUS data, in accordance with at least one embodiment of the present disclosure. A current frame indicator 1215 shows where on the cartoon roadmap or virtual venogram 500 of the vasculature the transducer array 124 of the catheter 510 is presently located. Label presets 1220 are also provided (e.g., vasculature segment abbreviations such as CIV, EIV, CFV, etc.). The IVUS frames are automatically labeled based on image analysis. In this example, the current position of the transducer array has been identified as the exterior iliac vein 550, and so the EIV label preset 1220 is highlighted or illuminated. A pullback speed indicator 1230 provides guidance to the clinician or other user for a stable pullback speed. The pullback speed indicator 1230 can be a series of blocks that are filled based on the speed (e.g., more blocks indicate faster speed and fewer blocks indicate slower speed). A tomographic IVUS image 1010 shows the current frame, and an automatic label 1240 can be generated using image analysis with the label presets described with respect to the current frame indicator 1215, e.g., by the vasculature segment abbreviation. Bookmark thumbnails 1250 appear when the user presses the bookmark option and/or the label preset option. A direction indicator 1260 is also included, showing, e.g., the orientation or direction of movement of the transducer array. Anterior (A), posterior (P), medial (M), lateral (L), and/or other suitable direction labels can be used. The direction indicator can include a compass arrow that moves based on the direction of movement. Interesting anatomy 1270 (e.g., thrombus) within the IVUS image 1010 can be colored, shaded, and/or highlighted.

Figure 13:
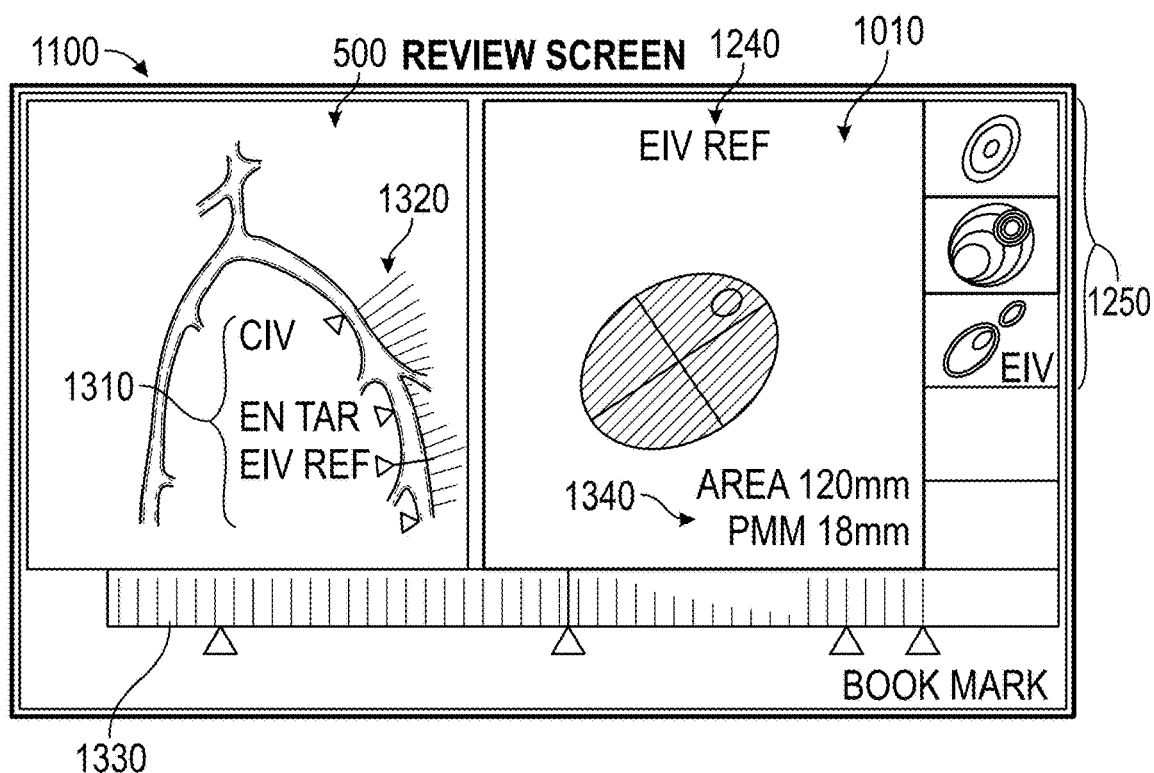
FIG. 13 illustrates a screen display during review of the IVUS images obtained during the pullback.

FIG. 13 illustrates a screen display during review of the IVUS images obtained during the pullback. The roadmap, longitudinal image, or virtual venogram 500 of the vasculature shows all of the bookmarked frames and labels 1310 (e.g., vasculature segment abbreviation, target frame, reference frame, frame representative of diseased or compressed vasculature, frame representative of vasculature that needs treatment, frame representative of healthy vasculature, etc.) The processing system 106 performs automatic image analysis of the obtained IVUS image data and calculates one or more metrics (e.g., cross-sectional lumen area, diameter, compression, plaque burden, etc.) A graphical representation 1320 of the automatically calculated metrics is shown on the roadmap image of the vasculature, e.g., adjacent to the vasculature. For example, the graphical representation can be a bar (such as in a bar graph) or a histogram representative of the value corresponding to adjacent portion of the vasculature. In some embodiments, two or more metrics can be displayed (e.g., in different colors). An alternative view 1330 of the graphical representation of the one or more metrics is also shown. For example, the graphical representation extends length-wise along the screen display, rather than adjacent to the vasculature in the roadmap image. Any suitable graphical representation, such as a line graph, a bar graph, symbols can be used to represent the metrics 1320 on the roadmap image or the alternative view of the metrics 1330. The tomographic IVUS image 1010 can be automatically assigned a label 1240 using image analysis with the label presets (e.g., vasculature segment name, reference frame, target frame, etc.). The tomographic IVUS image frame 1010 can also include a visual representation 1340 of one or more calculated metrics for that image frame (e.g., numerical values of cross-sectional lumen area, diameter). The bookmark video thumbnails 1250 are provided on the screen display 1100, adjacent to, e.g., tomographic IVUS image 1010. The user is able to click on a thumbnail 1250 to play the corresponding video with multiple IVUS image frames 1010. The user can select a representative IVUS image frame 1010 from the video clip as the thumbnail. The thumbnail includes a label (e.g., vasculature segment name).

Figure 14:
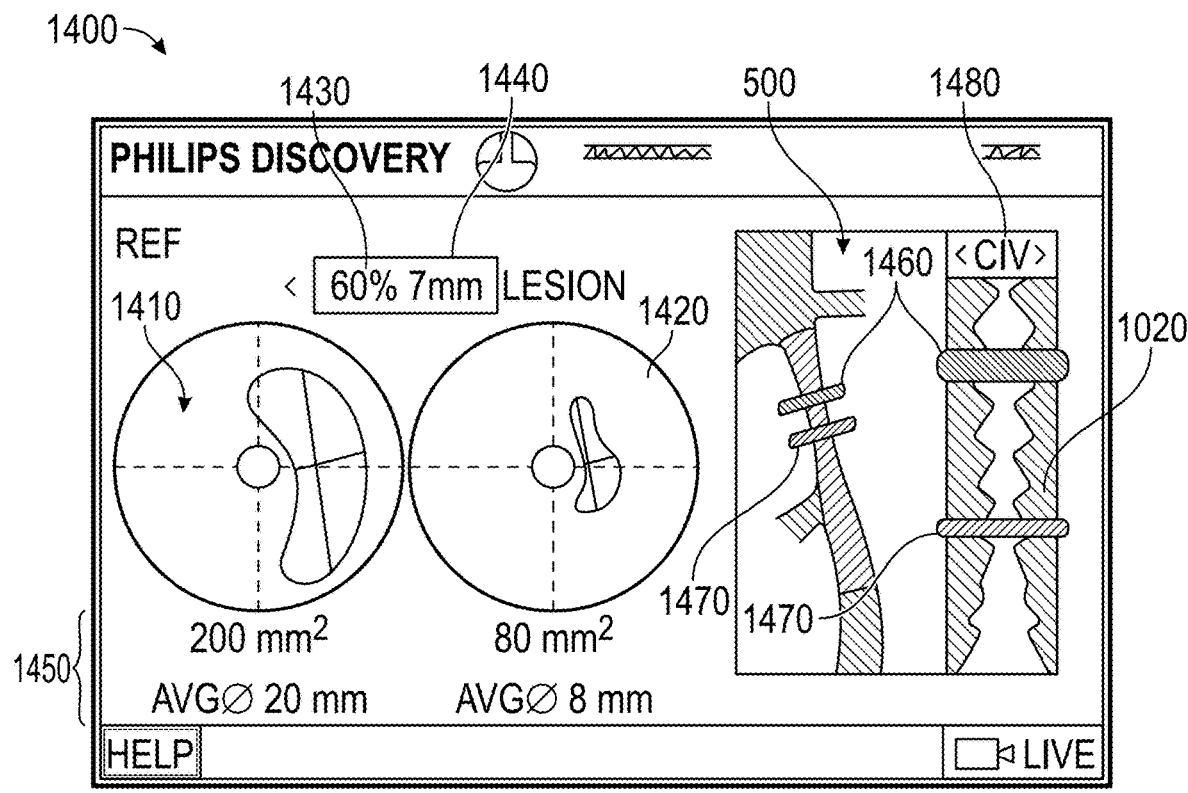
FIG. 14 shows a screen display for review of IVUS image data in accordance with at least one embodiment of the present disclosure.
Figure 15:
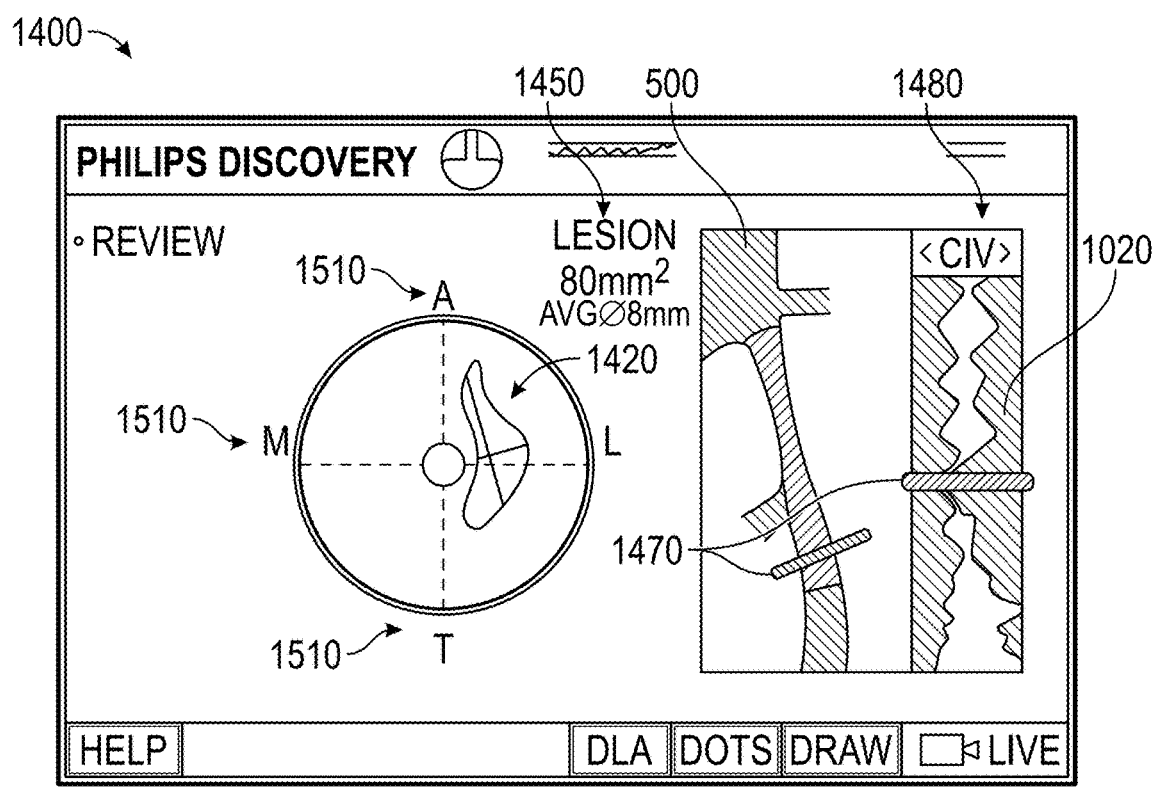
FIG. 15 shows a screen display for review of IVUS image data in accordance with at least one embodiment of the present disclosure.
Figure 16:
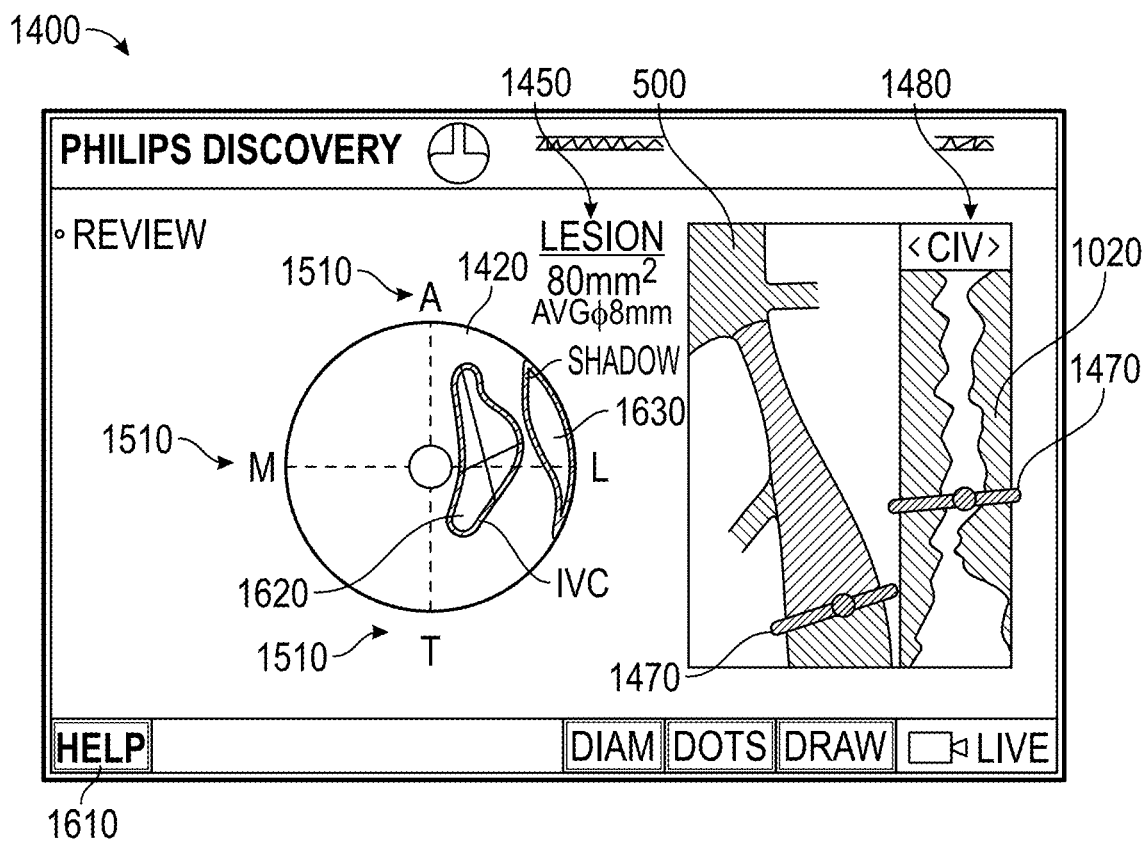
FIG. 16 shows a screen display for review of IVUS image data in accordance with at least one embodiment of the present disclosure.

FIGS. 14-16 illustrates screen displays providing the user review of IVUS image data obtained during a pullback in peripheral vasculature. The screen displays provide: relevant metrics are shown automatically, autodetection of other elements when needed, and vertical ILD.

FIG. 14 shows a screen display 1400 for review of IVUS image data in accordance with at least one embodiment of the present disclosure. On the left side of the screen display, two IVUS image frames are displayed (e.g., a reference frame 1410 and a lesion frame 1420). On completion of the pullback, the processing system 106 will automatically calculate, using image analysis, and display the percentage of compression 1430 in the vasculature segment. The length 1440 of the lesion is also calculated with image analysis and displayed. Other metrics 1450, such as the cross-sectional lumen area and/or the diameter corresponding to the two frames, are also automatically calculated and displayed. In some instances, an average value is calculated and displayed. On the right side of the screen display, a co-registered venogram or virtual venogram 500 showing the vasculature segment containing the displayed IVUS image frames 1410 and 1420 is shown. Markers 1460 and 1470 are provided on the venogram 500 to show the locations of the reference and lesion IVUS image frames 1410 and 1420. The right side of the screen display also includes a vertical ILD 1020 of the vasculature segment. It should be understood that in other examples or embodiments, the vertical ILD 1020 may be located elsewhere on the screen display 1400. The vertical ILD 1020 can be made of the of the IVUS image frames 1010 obtained during the pullback. A label (e.g., abbreviation of vasculature segment, such as CIV) is also shown. Markers are also provided on the vertical ILD to show the locations of the reference and lesion IVUS image frames.

FIG. 15 shows a screen display 1400 for review of IVUS image data in accordance with at least one embodiment of the present disclosure. The user can click on a tomographic IVUS image frame 1410 or 1420 from FIG. 14 to enlarge it. For example, the lesion frame 1420 from FIG. 14 is shown to be enlarged in FIG. 15. The user can edit the measurements (e.g., by selecting the lumen border using dots around the lumen or drawing a line around the lumen, the orientation of the diameter line) on the enlarged IVUS image frame. Direction labels 1510 (e.g., A, P, M, L) are provided around the IVUS image 1420. A marker 1470 showing the location of the selected frame 1420 is provided in the venogram 500 and the vertical ILD 1020 on the right side of the screen display.

FIG. 16 shows a screen display 1400 for review of IVUS image data in accordance with at least one embodiment of the present disclosure. The user can select the help option 1610, which causes the processing system 106 to auto segment elements in the tomographic IVUS image 1420 and/or label the elements. For example, the automatic segmentation identifies and labels the lumen border of the vasculature segment 1620 (inferior vena cava or IVC) and a shadow 1630 in the tomographic image 1420.

Figure 17:
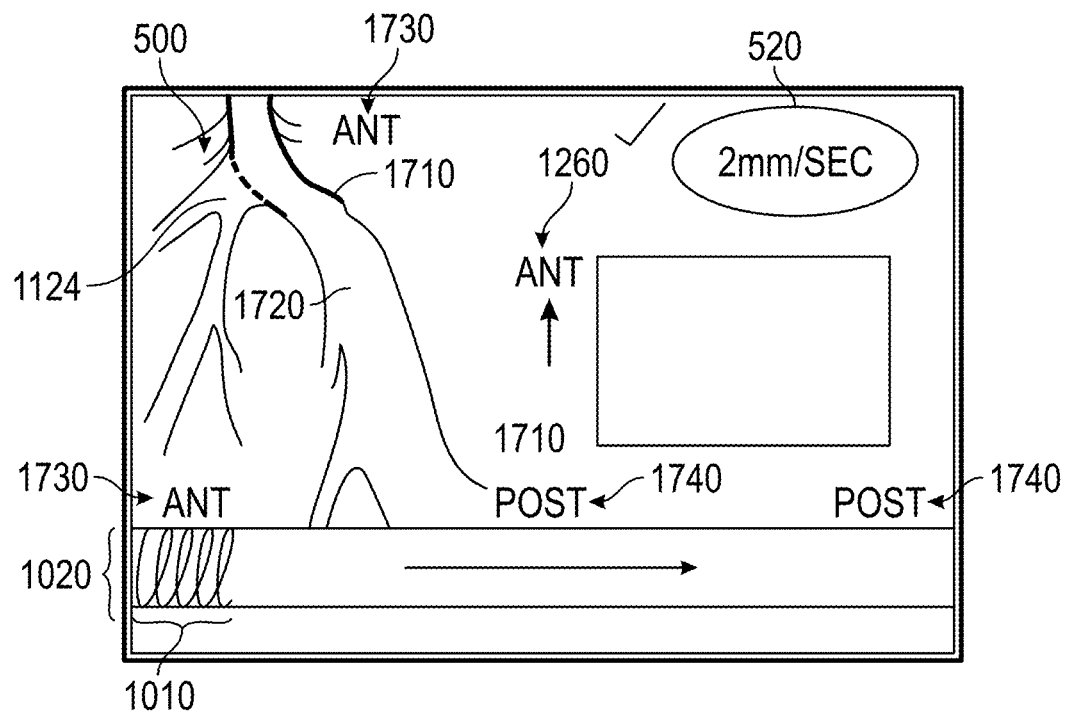
FIG. 17 illustrates a screen display during pullback, e.g., during recording of IVUS data, in accordance with at least one embodiment of the present disclosure.
Figure 18:
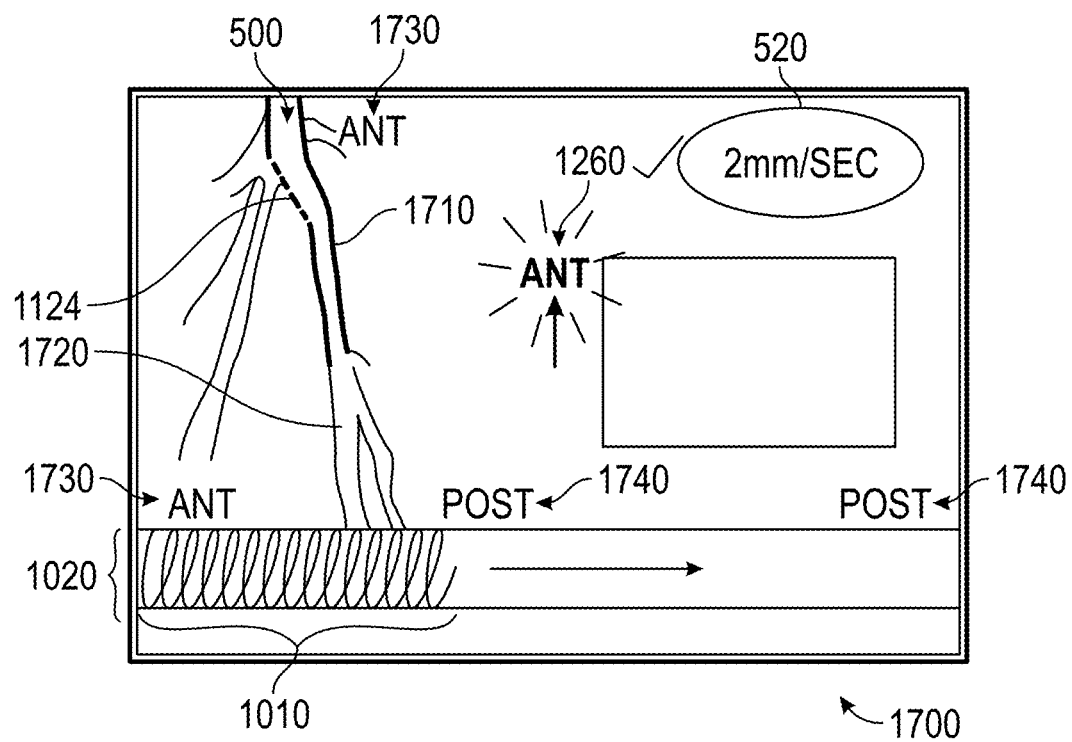
FIG. 18 illustrates an example screen display during a later stage of an IVUS pullback, in accordance with at least one embodiment of the present disclosure.
Figure 19:
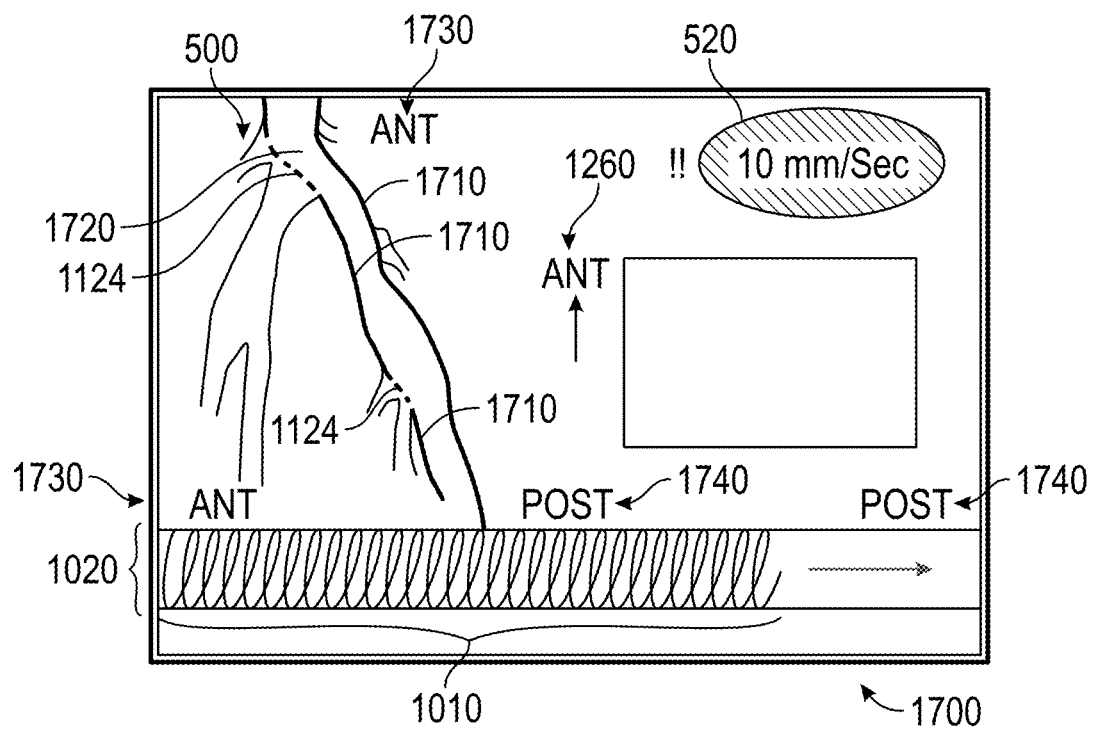
FIG. 19 illustrates an example screen display at or near the end of the IVUS pullback, in accordance with at least one embodiment of the present disclosure.

FIGS. 17-19 illustrates screen displays providing the user guidance during an IVUS pullback in peripheral vasculature. The screen displays provide: speed indicators for pullback, speed gauge, map of vasculature is built during pullback (e.g., fill the map as you go), display of directional label (e.g., anterior) and/or arrow. In general, the map or image of the vasculature may be a 2D or 3D graphical representation.

FIG. 17 illustrates a screen display 1700 during pullback, e.g., during recording of IVUS data, in accordance with at least one embodiment of the present disclosure. On the left side of the screen display, a roadmap image, co-registered external image, or virtual venogram 500 of the vasculature is shown. A portion 1710 of the vasculature 1720 from which IVUS data has already been collected is highlighted, colored, and/or shaded. For example, the vessel boundary in the region 1710 where pullback has already occurred is bolded, while the other areas of the vessel 1720 are shown more lightly. A solid bold line 1710 can be used for the vessel boundary, while a dashed bold line 1124 can be used when crossing a branching vessel. More and more of the vessel 1720 is visually accentuated 1710 as the pullback progresses. In that regards, the map 500 of the vasculature 1720 is built during the pullback. The anterior (ANT) and posterior (POST) portions 1730 and 1740 of the vasculature are labeled on the roadmap image 500, with pullback occurring with the transducer array 124 being moved longitudinally from the anterior portion 1730 to posterior portion 1740. Along the bottom of the display, a horizontal ILD 1020 is shown. It should be understood that in other examples or embodiments, the horizontal ILD 1020 may be located elsewhere within the screen display 1700. The ILD 1020 is formed from the IVUS data during the pullback. As shown, the ILD 1020 is also built during the pullback, with more and more IVUS image frames 1010 being added to the ILD 1020 as the pullback progresses. The anterior (ANT) and posterior (POST) portions 1730 and 1740 of the vasculature 1720 are labeled on the roadmap image 500. A compass 1260 is provided in the middle of the screen display 1700, although it can be located elsewhere on the screen display 1700. For example, the anterior direction (ANT) can always be on top (e.g., the 12 o'clock position). The compass arrow 1260 can change directions based on the orientation or direction of movement of the transducer array within the vasculature 1720 during the pullback. A pullback speed indicator 520 is provided on the top right of the screen display. The pullback speed indicator 520 can display the speed of the manual pullback with a numerical value. The indicator can also include a graphical representation (e.g., a symbol) of whether the speed is too fast, too slow, or correct. For example, a checkmark can indicate that the pullback speed is correct.

FIG. 18 illustrates an example screen display 1700 during a later stage of an IVUS pullback, in accordance with at least one embodiment of the present disclosure. As shown on the virtual venogram 500 of the left side of the screen display 1700, a greater length of the vasculature 1720 has been highlighted (1710, 1124) as compared to FIG. 17, indicating that IVUS data has been obtained from a greater length of the vasculature 1720. Similarly, a greater length of the ILD 1020 has been filled in with the obtained IVUS image frames 1010. The direction label (ANT) of the compass 1260 or the arrow of the compass 1260 can blink when the computer or processor is unsure of the direction the transducer array 124 is moving or oriented within the vasculature, or when the direction/orientation is being recalculated.

FIG. 19 illustrates an example screen display 1700 at or near the end of the IVUS pullback, in accordance with at least one embodiment of the present disclosure. As shown on the virtual venogram 500 at the left side of the screen display 1700, all or nearly all of the length of the vasculature 1720 under investigation has been highlighted (1710, 1124), indicating that IVUS data 1010 has been obtained from almost the complete length. Similarly, all or nearly all of the length of the ILD 1020 has been filled in with the obtained IVUS image frames 1010. The pullback speed indicator 520 on the top right of the screen display 1700 shows that the pullback speed is too high. For example, symbols (e.g., exclamation marks) and/or coloring (e.g., red) of the numerical speed value can be used to indicate to the user that the pullback speed should be slowed down.

Figure 20:
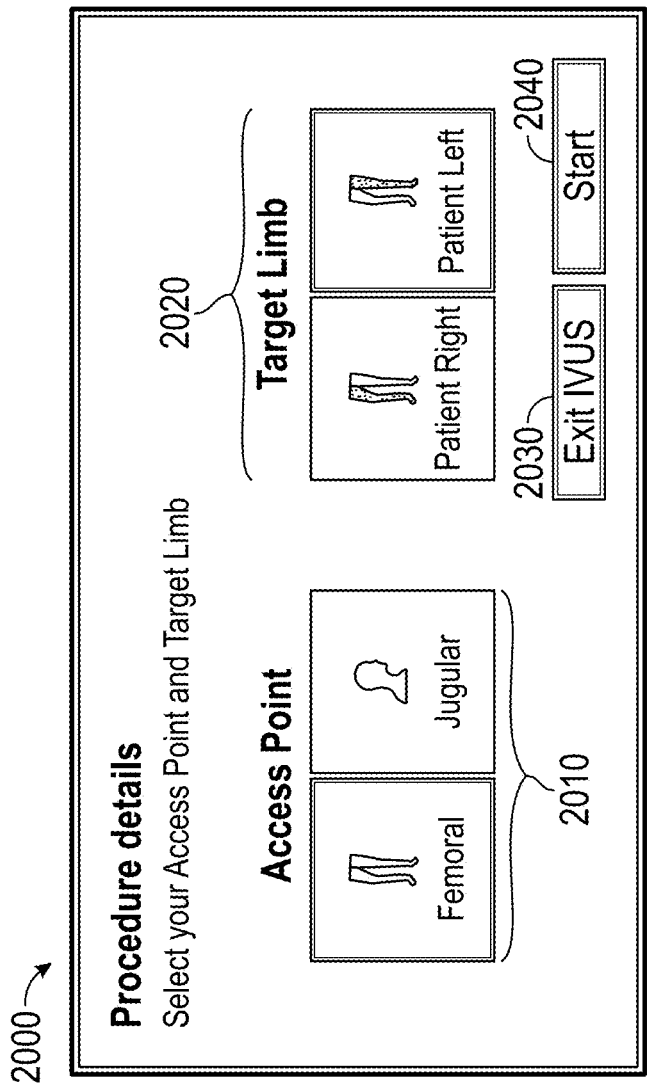
FIG. 20 is a screenshot of an IVUS access point selection screen, in accordance with at least one embodiment of the present disclosure.

FIG. 20 is a screenshot of an IVUS access point selection screen 2000, in accordance with at least one embodiment of the present disclosure. The IVUS pullback virtual venogram system may be generally capable of automatically identifying different regions of a patient's circulatory system by using a machine-learning algorithm or other training-based AI algorithm to match IVUS images against an a priori dataset or knowledge set of statistically representative lumen anatomy for different human subpopulations. However, the accuracy of vessel identification is improved when the IVUS pullback virtual venogram system begins with accurate and specific information about the starting point and direction of travel of the ultrasound transducer 124 of the imaging catheter 510. In this example, the screen display 2000 therefore includes an access point selector 2010 that permits a clinician or other user to select between femoral access and jugular access. The screen display 2000 also includes a target limb selector 2020 that permits a clinician or other user to select between a patient's right leg and left leg as the location of the IVUS pullback. These examples are merely illustrative; other access points and target limbs or target regions are also possible and may be used instead or in addition, depending on the procedure type, disease type, and location of the anatomical features of interest.

Also visible are an exit button 2030 and a start button 2040. Other controls may also be provided including but not limited to help buttons, procedure type selectors, disease type selectors, and anatomy type selectors.

Figure 21:
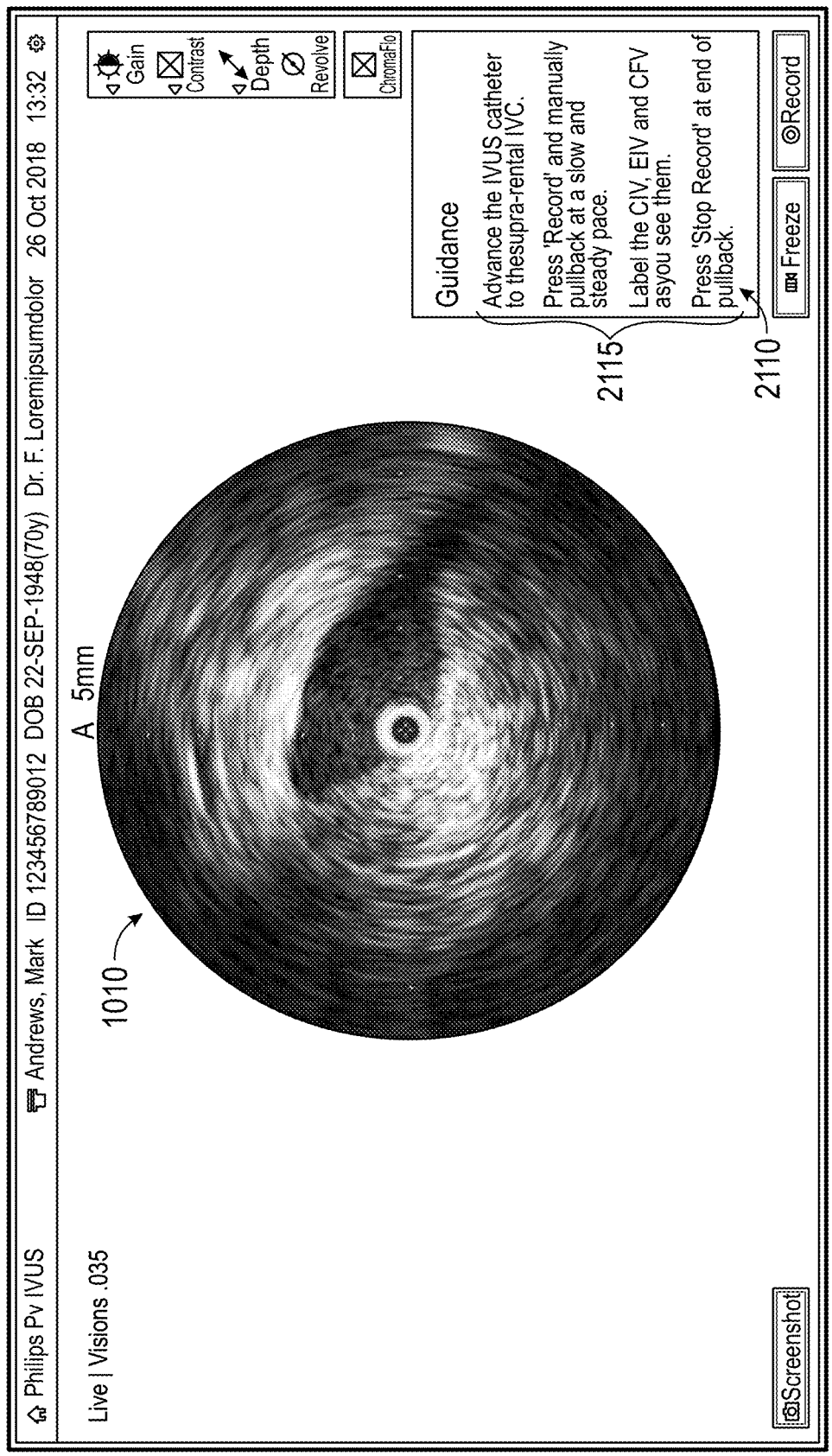
FIG. 21 is a screenshot of a user guidance screen display, in accordance with at least one embodiment of the present disclosure.

FIG. 21 is a screenshot of a user guidance screen display 2100, in accordance with at least one embodiment of the present disclosure. Visible are a tomographic IVUS image 1010 and a guidance pane 2110. In this example, the guidance pane 2110 displays specific instructions 2115 to the user on the operation of both the imaging catheter 510 and the IVUS pullback virtual venogram system. These instructions 2115 reduce the training and memorization burden on the clinician or other user, by reducing the need to be familiar with the specifics of a given system.

Figure 22:
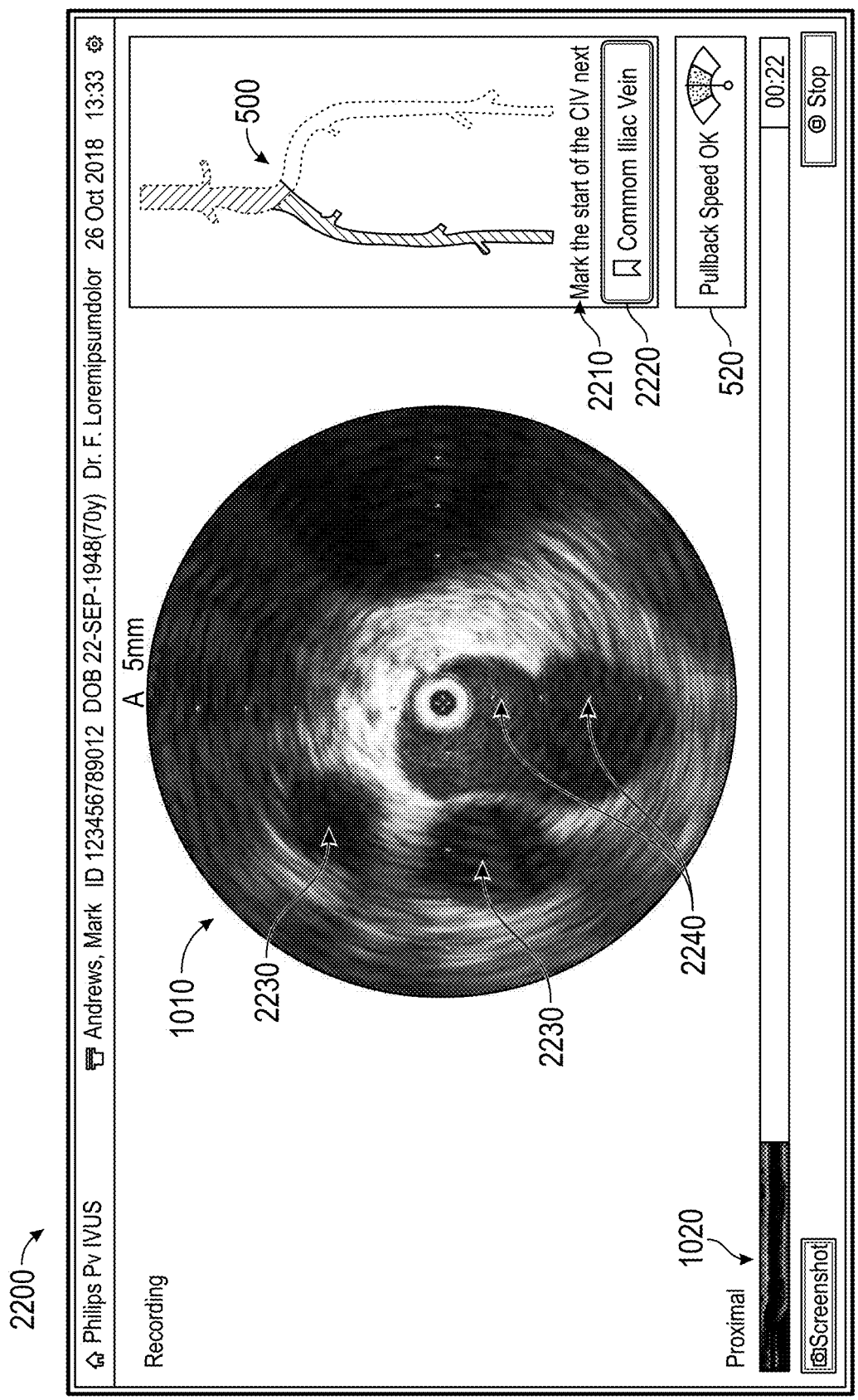
FIG. 22 is a screenshot of a pullback navigation and marking display, in accordance with at least one embodiment of the present disclosure.

FIG. 22 is a screenshot of a pullback navigation and marking display 2200, in accordance with at least one embodiment of the present disclosure. The screen display 2200 includes a live tomographic IVUS image 1010, image longitudinal display (ILD) 1020, virtual venogram 500, pullback speed indicator 520, user instruction 2210, and labeling button 2220. In this example, the user instruction 2210 is instructing the user to click the labeling button 2220 when the pullback of the ultrasound transducer array 124 reaches the start of the common iliac vein. In some embodiments, this selection is optional, as the IVUS pullback virtual venogram system identifies the start and end of different vasculature segments automatically. In other embodiments, the IVUS pullback virtual venogram system permits the clinician or other user to select the marking of the start or end of a vasculature segment through voice, gesture, or other touch-free command, such that a non-sterile staff member is not needed to operate a keyboard, mouse, joystick, or other non-sterile input device.

In this example, the IVUS image 1010 shows a bifurcating artery 2230 and a bifurcating vein 2240. The size and locations of these bifurcations may be important for the image recognition algorithm to identify the beginning and end of different vasculature segments within the patient's body.

Figure 23:
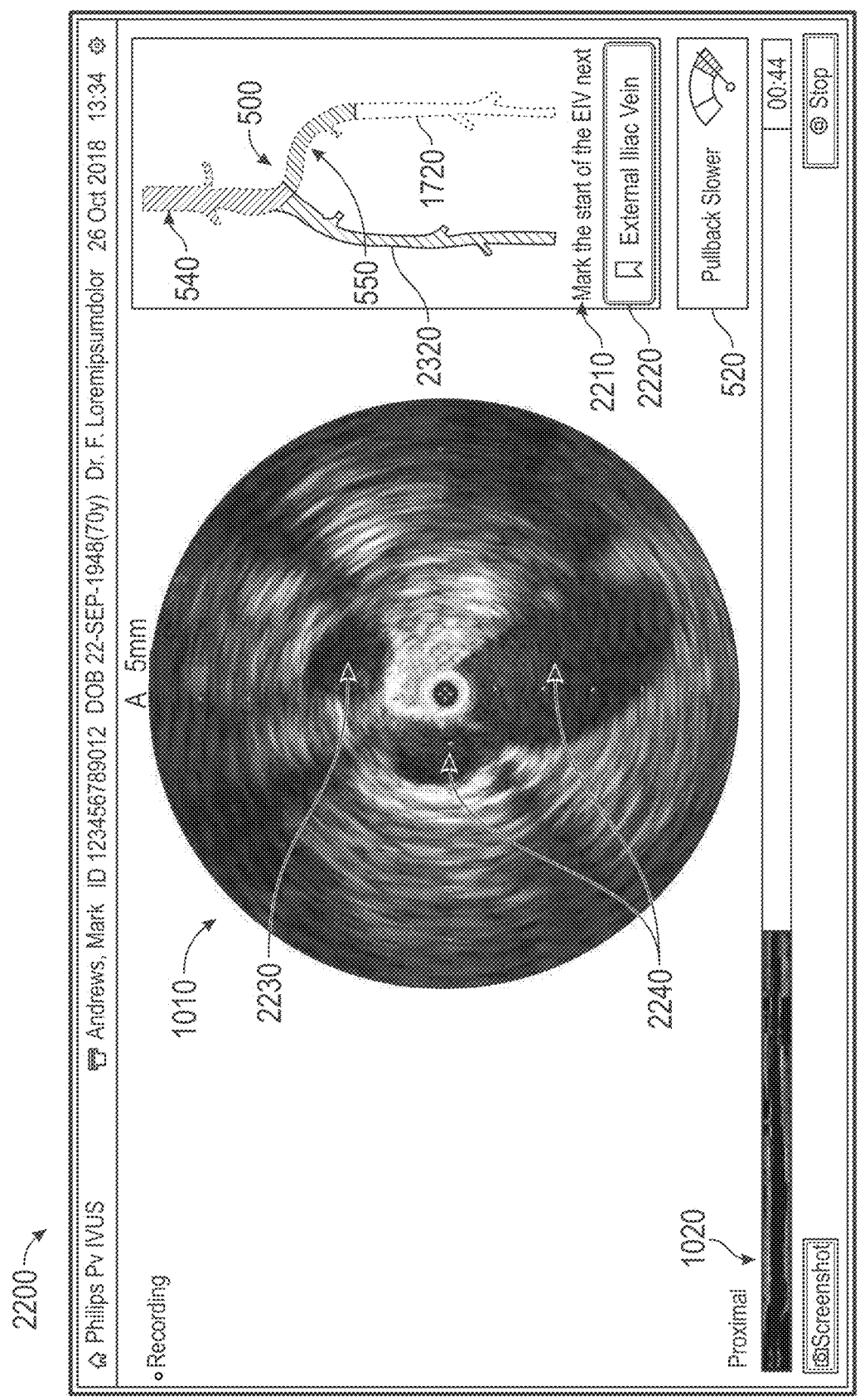
FIG. 23 is a screenshot of a pullback navigation and marking display, in accordance with at least one embodiment of the present disclosure.

FIG. 23 is a screenshot of a pullback navigation and marking display 2200, in accordance with at least one embodiment of the present disclosure. Visible are the live tomographic IVUS image 1010, image longitudinal display (ILD) 1020, virtual venogram 500, pullback speed indicator 520, one-line user instruction 2210, labeling button 2220, artery 2230 (no longer bifurcating but now joined into a single lumen), and bifurcating vein 2240. In this example, the common iliac vein (CIV) 540 has been marked and highlighted on the virtual venogram, indicating that this is the segment of the patient's vasculature presently occupied by the ultrasound imaging array 124. In this example, the right external iliac vein (EIV) 550 is marked in a different color (e.g., light gray) to indicate this is the next segment the imaging array 124 will enter. The rest of the right-leg vasculature 1720 is marked with dotted lines, to show that it is not currently involved in the pullback procedure, while the left leg vasculature 2320 is grayed out (e.g., displayed with a gray color close to the background color) to indicate that it will not be involved in the pullback procedure at all.

Figure 24:
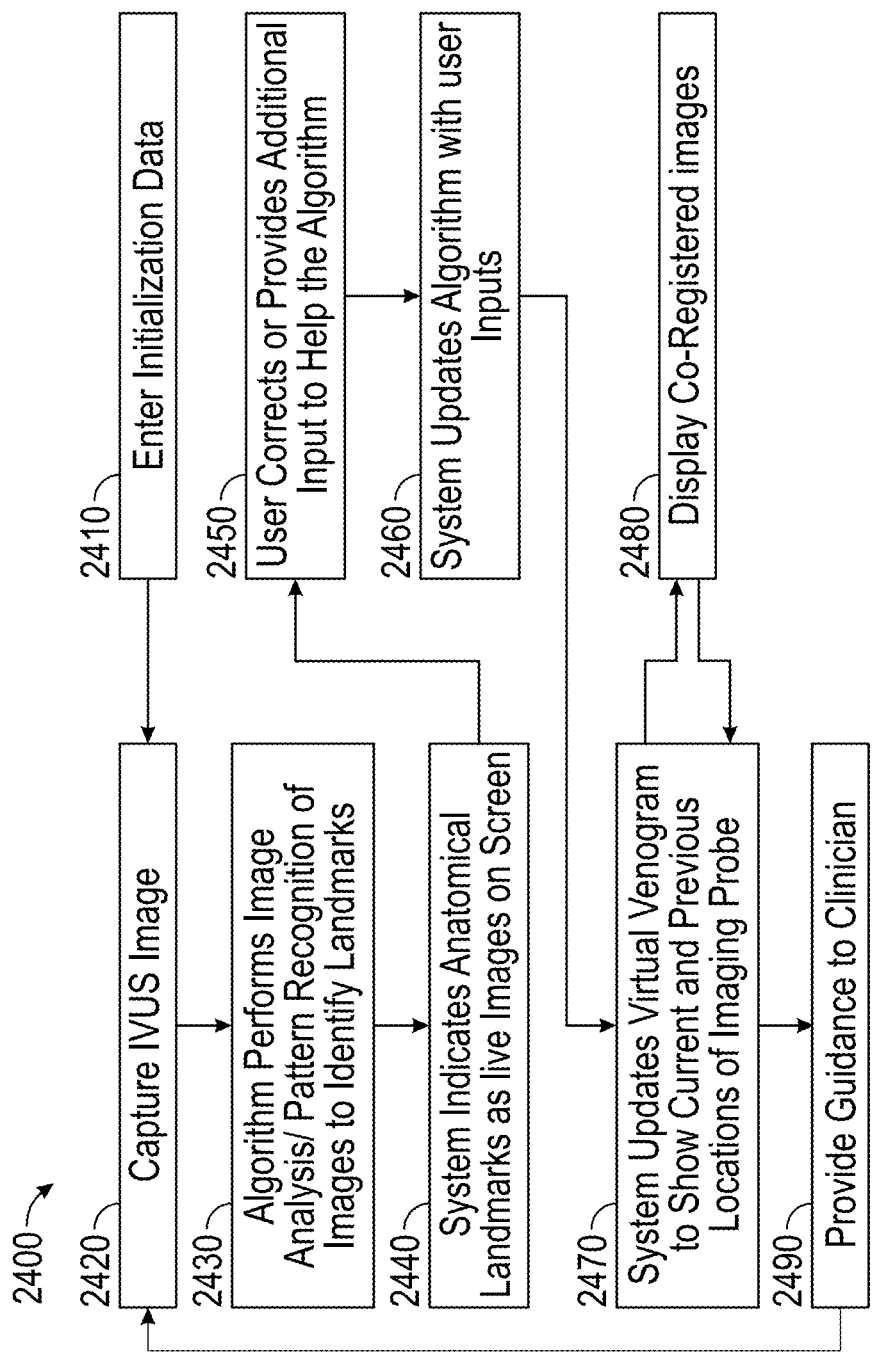
FIG. 24 illustrates a flow diagram for an example intraluminal directional guidance method, in accordance with aspects of the present disclosure.

FIG. 24 illustrates a flow diagram for an example intraluminal directional guidance method 2400, in accordance with aspects of the present disclosure. It is understood that the steps of method 2400 may be performed in a different order than shown in FIG. 13, additional steps can be provided before, during, and after the steps, and/or some of the steps described can be replaced or eliminated in other embodiments. These steps may be executed for example as coded instructions on a processor such as processing system 106 of FIG. 1, and displayed for example on monitor 108 of FIG. 1, in response to inputs by a clinician or other user.

In step 2410, the user initializes the intraluminal directional guidance system with directional information at the start of a procedure (e.g., an IVUS pullback procedure) as shown for example in FIG. 20. This information may include for example the entry point or access point into the body (e.g., jugular, radial, right or left femoral) and the target anatomy or direction of movement. This information may be used by the system to select specific algorithms, data sets, or body regions for image recognition.

In step 2420, the IVUS imaging system 100 captures an IVUS image. Such images may be captured either discretely or continuously during a procedure (e.g., a pullback procedure), and stored within a memory of the processing system 106.

In step 2430, the processor 106 performs border detection, image processing, image analysis, and pattern recognition of the captured IVUS image to identify anatomical landmarks (e.g., specific veins, and branching points between veins). While the pullback run is performed, the algorithm detects these landmarks based on a-priori information of the venous system geometry. Such analysis and recognition may rely on conventional techniques, or may be training-based or learning-based (e.g., incorporating machine learning, deep learning, or other related artificial intelligence). In some embodiments, information from external images, when available, may be incorporated into the image recognition algorithm, such that a patient's own unique anatomy is considered. In other embodiments or circumstances, the pattern recognition algorithms may search for analogues of statistically representative lumen anatomy for a given subpopulation, or such statistically representative lumen anatomy may be used to train the algorithm or algorithms. Examples of border detection, image processing, image analysis, and/or pattern recognition include U.S. Pat. No. 6,200,268 entitled "VASCULAR PLAQUE CHARACTERIZATION" issued Mar. 13, 2001 with D. Geoffrey Vince, Barry D. Kuban and Anuja Nair as inventors, U.S. Pat. No. 6,381,350 entitled "INTRAVASCULAR ULTRASONIC ANALYSIS USING ACTIVE CONTOUR METHOD AND SYSTEM" issued Apr. 30, 2002 with Jon D. Klingensmith, D. Geoffrey Vince and Raj Shekhar as inventors, U.S. Pat. No. 7,074,188 entitled "SYSTEM AND METHOD OF CHARACTERIZING VASCULAR TISSUE" issued Jul. 11, 2006 with Anuja Nair, D. Geoffrey Vince, Jon D. Klingensmith and Barry D. Kuban as inventors, U.S. Pat. No. 7,175,597 entitled "NON-INVASIVE TISSUE CHARACTERIZATION SYSTEM AND METHOD" issued Feb. 13, 2007 with D. Geoffrey Vince, Anuja Nair and Jon D. Klingensmith as inventors, U.S. Pat. No. 7,215,802 entitled "SYSTEM AND METHOD FOR VASCULAR BORDER DETECTION" issued May 8, 2007 with Jon D. Klingensmith, Anuja Nair, Barry D. Kuban and D. Geoffrey Vince as inventors, U.S. Pat. No. 7,359,554 entitled "SYSTEM AND METHOD FOR IDENTIFYING A VASCULAR BORDER" issued Apr. 15, 2008 with Jon D. Klingensmith, D. Geoffrey Vince, Anuja Nair and Barry D. Kuban as inventors and U.S. Pat. No. 7,463,759 entitled "SYSTEM AND METHOD FOR VASCULAR BORDER DETECTION" issued Dec. 9, 2008 with Jon D. Klingensmith, Anuja Nair, Barry D. Kuban and D. Geoffrey Vince, as inventors, the teachings of which are hereby incorporated by reference herein in their entirety.

In step 2440, the processor indicates the identified anatomical landmarks, or other outcomes of image analysis such as borders, segments, etc., to the user, e.g., as annotations or overlays on the live image data displayed on the monitor 108.

In step 2450, the processor 106 is receptive to optional additional inputs from the user, comprising information to assist the pattern recognition algorithm. For example, if the user believes the identification displays of step 2440 are incorrect, incomplete, mis-located or otherwise in need of correction, the user may optionally correct this information using a keyboard, mouse, joystick, trackball, or other user input device communicatively connected to the processing system 106.

In step 2460, if the user has entered such corrections during step 2550, the processing system 106 updates the information located within the algorithm to reflect the corrections. Optionally, the processing system 106 may also upload the corrections to a central server, cloud server, or other remote site, such that they may be incorporated into new training sets for machine learning algorithms and then distributed to other users.

In step 2470, the processing system updates the virtual venogram 500 to show the current and previous locations of the imaging probe, as shown for example in FIGS. 5-10, 12-19, and 22-23.

In step 2480, the processing system 106 displays on the display a co-registered image, if available, and if selected to do so by an appropriate user input (e.g., the co-registration button 656 shown in FIG. 6). Such co-registered images may include for example an X-ray, fluoroscopy, CAT scan, external ultrasound, or other image captured by the external imaging system 132 and showing, for example, vasculature or other anatomy in the vicinity of the intravascular imaging probe 102.

In some embodiments, co-registered images, when available, may also be incorporated into the image recognition algorithm.

In step 2490, if an appropriate user input has been selected, the processing system 106 provides guidance to the clinician regarding movements of the intravascular imaging probe controls 104 that may be required to advance or retract the probe 102 to a desired location within the patient's body, or to mark the start or end of a given vascular segment, or to start or stop recording. Such guidance may be determined through conventional techniques (e.g., database lookup) or through learning-based techniques.

A person or ordinary skill in the art will understand that for some embodiments, one or more of the above steps could be eliminated or performed in a different sequence, and that other steps may be added. For example, in some embodiments, the system operates in a fully autonomous mode, requiring no input from the user. In some embodiments, the image recognition and landmark identification algorithms incorporate information from external images. In some embodiments, the system allows IVUS to be used by itself, without a need for external images to provide orientation information or clinician roadmaps.

In some embodiments, the system can also automatically detect and highlight neighboring landmarks (e.g., arteries or other vessels not under investigation) or other areas of interest (e.g., constrictions in neighboring vessels) as the imaging proceeds. Collectively, the features described above enable the system to group and label all IVUS frames between landmarks as belonging to a particular named segment of the patient's vasculature. The system accordingly auto computes the relevant metrics for diagnosis for that segment, e.g. compression, highlights areas of attention, and indicates the relative anatomical position of an IVUS frame. In other embodiments, the user can bookmark confluences, references points and healthy areas by vocal command, thus avoiding the need for a non-sterile staff member to push a button on the touchscreen.

In other embodiments, the virtual venogram is a 3D reconstruction of the real patient vessel anatomy, as obtained from segmentation of a CT or MR angiography study. This data can be loaded onto the IVUS system from the hospital picture archiving and communication system (PACS), offering the advantage of taking into account real patient anatomy and thus correct positions of vascular segments. In other embodiments, the segments are automatically labeled also on the fluoroscopy screen, when co-registration between IVUS and the fluoroscopy system is enabled. Applications for the IVUS pullback virtual venogram system include IVUS education, the use of IVUS systems for treating Peripheral Vascular (PV) disease, and links to other vessel navigation and visualization systems such as Philips' Vessel Navigator.

Figure 25:
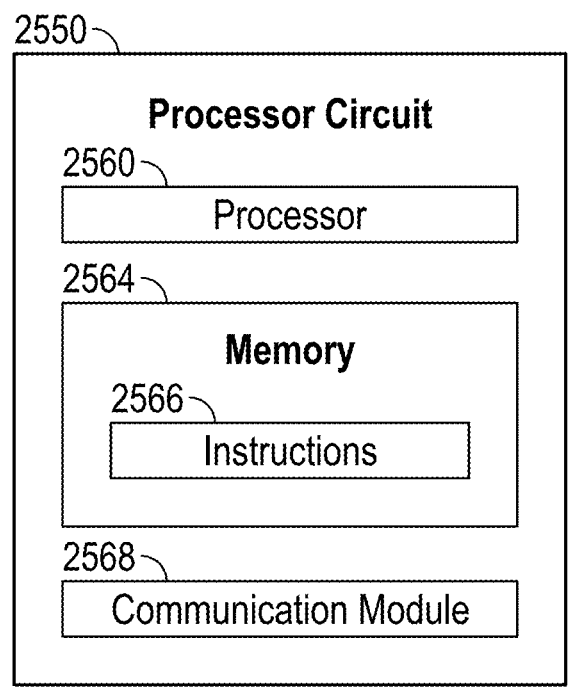
FIG. 25 is a schematic diagram of a processor circuit, according to embodiments of the present disclosure.

FIG. 25 is a schematic diagram of a processor circuit 2550, according to embodiments of the present disclosure. The processor circuit 2550 may be implemented in the ultrasound imaging system 100, or other devices or workstations (e.g., third-party workstations, network routers, etc.), or in a cloud processor or other remote processing unit, as necessary to implement the method. As shown, the processor circuit 2550 may include a processor 2560, a memory 2564, and a communication module 2568. These elements may be in direct or indirect communication with each other, for example via one or more buses.

The processor 2560 may include a central processing unit (CPU), a digital signal processor (DSP), an ASIC, a controller, or any combination of general-purpose computing devices, reduced instruction set computing (RISC) devices, application-specific integrated circuits (ASICs), field programmable gate arrays (FPGAs), or other related logic devices, including mechanical and quantum computers. The processor 2560 may also comprise another hardware device, a firmware device, or any combination thereof configured to perform the operations described herein. The processor 2560 may also be implemented as a combination of computing devices, e.g., a combination of a DSP and a microprocessor, a plurality of microprocessors, one or more microprocessors in conjunction with a DSP core, or any other such configuration.

The memory 2564 may include a cache memory (e.g., a cache memory of the processor 2560), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 2564 includes a non-transitory computer-readable medium. The memory 2564 may store instructions 2566. The instructions 2566 may include instructions that, when executed by the processor 2560, cause the processor 2560 to perform the operations described herein. Instructions 2566 may also be referred to as code. The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may include a single computer-readable statement or many computer-readable statements.

The communication module 2568 can include any electronic circuitry and/or logic circuitry to facilitate direct or indirect communication of data between the processor circuit 2550, and other processors or devices. In that regard, the communication module 2568 can be an input/output (I/O) device. In some instances, the communication module 2568 facilitates direct or indirect communication between various elements of the processor circuit 2550 and/or the ultrasound imaging system 100. The communication module 2568 may communicate within the processor circuit 2550 through numerous methods or protocols. Serial communication protocols may include but are not limited to US SPI, I²C, RS-232, RS-485, CAN, Ethernet, ARINC 429, MODBUS, MIL-STD-1553, or any other suitable method or protocol. Parallel protocols include but are not limited to ISA, ATA, SCSI, PCI, IEEE-488, IEEE-1284, and other suitable protocols. Where appropriate, serial and parallel communications may be bridged by a UART, USART, or other appropriate subsystem.

External communication (including but not limited to software updates, firmware updates, preset sharing between the processor and central server, or readings from the ultrasound device) may be accomplished using any suitable wireless or wired communication technology, such as a cable interface such as a USB, micro USB, Lightning, or FireWire interface, Bluetooth, Wi-Fi, ZigBee, Li-Fi, or cellular data connections such as 2G/GSM, 3G/UMTS, 4G/LTE/WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information. Information may also be transferred on physical media 610 such as a USB flash drive or memory stick.

A number of variations are possible on the examples and embodiments described above. For example, the IVUS pullback virtual venogram system may be employed in anatomical systems within the body other than those described, or may be employed to image other disease types, object types, or procedure types than those described. The technology described herein may be applied to intraluminal imaging sensors of diverse types, whether currently in existence or hereinafter developed.

Accordingly, the logical operations making up the embodiments of the technology described herein are referred to variously as operations, steps, objects, elements, components, or modules. Furthermore, it should be understood that these may be performed in any order, unless explicitly claimed otherwise or a specific order is inherently necessitated by the claim language. All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the IVUS pullback virtual venogram system. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." Unless otherwise noted in the claims, stated values shall be interpreted as illustrative only and shall not be taken to be limiting.

The above specification, examples and data provide a complete description of the structure and use of exemplary embodiments of the IVUS pullback virtual venogram system as defined in the claims. Although various embodiments of the claimed subject matter have been described above with a certain degree of particularity, or with reference to one or more individual embodiments, those skilled in the art could make numerous alterations to the disclosed embodiments without departing from the spirit or scope of the claimed subject matter. Still other embodiments are contemplated. It is intended that all matter contained in the above description and shown in the accompanying drawings shall be interpreted as illustrative only of particular embodiments and not limiting. Changes in detail or structure may be made without departing from the basic elements of the subject matter as defined in the following claims.

What is claimed is:

1. An intravascular imaging system, comprising:
an intravascular imaging catheter; and
a processor circuit configured for communication with the intravascular imaging catheter, wherein the processor circuit is configured to:
output, to a display in communication with the processor circuit, a screen display during live imaging by the intravascular imaging catheter, wherein the screen display comprises:
a live intravascular image obtained by the intravascular imaging catheter;
a stylized diagram of a blood vessel of a patient, wherein the blood vessel comprises a continuous length formed by a plurality of named segments, wherein the plurality of named segments comprises a first named segment and a second named segment, wherein the first named segment in the stylized diagram comprises a first visual appearance; and
a first instruction for a user to perform an action at a time when an event occurs, wherein the action comprises applying a first named segment label, wherein the event comprises the live intravascular image depicting the first named segment;
modify the live intravascular image to be a first plurality of intravascular images as the first plurality of intravascular images is obtained by the intravascular imaging catheter during movement of the intravascular imaging catheter through the first named segment and the second named segment;
receive, during the movement, a first user input applying the first named segment label to a first intravascular image of the first plurality of intravascular images, wherein the first user input is received when the first intravascular image is displayed as the live intravascular image and the intravascular imaging catheter is positioned within the first named segment during the movement;

modify, in response to the first user input, the first named segment in the stylized diagram to have a different, second visual appearance such that the modification from the first visual appearance to the second visual appearance indicates that the intravascular imaging catheter is positioned within the first named segment during the movement.

2. The system of claim 1, wherein the screen display further comprises:

markers indicating proximal and distal boundaries of one or more of the plurality of named segments in the stylized diagram.

3. The system of claim 1, wherein the screen display further comprises:

a marker indicating a location of interest in the stylized diagram.

4. The system of claim 1, wherein the screen display further comprises:

one or more labels respectively identifying one or more named segments of the plurality of named segments in the stylized diagram.

5. The system of claim 1, wherein the screen display further comprises: a position indicator in the stylized diagram that indicates a location where the intravascular imaging catheter was located when the first plurality of intravascular images was obtained.

6. The system of claim 1, wherein the processor circuit is configured to receive a user input representative of where the intravascular imaging catheter was located when the first plurality of intravascular images was obtained.

7. The system of claim 1, wherein the screen display further comprises at least one of a longitudinal display of the blood vessel or a speed indicator associated with movement of the intravascular imaging catheter.

8. The system of claim 1, wherein the plurality of named segments comprises two or more of: inferior vena cava (IVC), common iliac vein (CIV), external iliac vein (EIV), common femoral vein (CFV), or femoral vein (F).

9. The system of claim 1, wherein a portion of the continuous length for the first named segment is defined based on a location of a branch extending from the blood vessel.

10. The system of claim 1, wherein each named segment of the plurality of named segments comprises a different portion of the continuous length, wherein the stylized diagram depicts a statistically representative shape that corresponds to a shape of the blood vessel such that the blood vessel is not directly displayed within the stylized diagram.

11. The system of claim 1, wherein the processor circuit is configured to:

modify, in response to the first user input, the screen display to include a second instruction for the user to perform a further action at a time when a further event occurs, wherein the further action comprises applying a second named segment label, wherein the further event comprises the live intravascular image depicting the second named segment.

12. The system of claim 11, wherein the processor circuit is configured to receive a user input identifying an access point for entry of the intravascular imaging catheter into the patient.

13. The system of claim 12, wherein the user input identifying the access point is representative of a direction of the movement of the intravascular imaging catheter within the blood vessel such that the screen display is configured to include the first instruction and the second instruction in a sequence based on the user input during the movement.

14. The system of claim 13, wherein the processor circuit is configured to automatically label the plurality of named segments in the stylized diagram.

15. The system of claim 1, wherein the processor circuit is configured to automatically annotate, in the stylized diagram, the plurality of named segments with a statistically representative reference value associated with a corresponding segment.

16. The system of claim 15, wherein the processor circuit is configured to automatically annotate, in the stylized diagram, the plurality of named segments with an automatically measured or calculated value associated with the corresponding segment.

17. The system of claim 16, wherein the processor circuit is configured to color the plurality of named segments based on a ratio of the automatically measured or calculated value to the statistically representative reference value.

18. The system of claim 11, wherein the second named segment in the stylized diagram comprises a third visual appearance, wherein the processor circuit is configured to:

modify, in response to the first user input, the second named segment in the stylized diagram to have a different, fourth visual appearance such that the modification from the third visual appearance to the fourth visual appearance indicates that the second named segment is a next segment within which the intravascular imaging catheter will be positioned.

19. An intravascular imaging method, comprising:

outputting, from a processor circuit in communication with an intravascular imaging catheter to a display in communication with the processor circuit, a screen display during live imaging by the intravascular imaging catheter, wherein the screen display comprises:

a live intravascular image obtained by the intravascular imaging catheter;

a stylized diagram of a blood vessel of a patient, wherein the blood vessel comprises a continuous length formed by a plurality of named segments, wherein the plurality of named segments comprises a first named segment and a second named segment, wherein the first named segment in the stylized diagram comprises a first visual appearance; and a first instruction for a user to perform an action at a time when an event occurs, wherein the action comprises applying a first named segment label, wherein the event comprises the live intravascular image depicting the first named segment;

modifying the live intravascular image to be a first plurality of intravascular images obtained by the intravascular imaging catheter during movement of the intravascular imaging catheter through the first named segment and the second named segment;

receiving, during the movement, a first user input applying the first named segment label to a first intravascular image of the first plurality of intravascular images, wherein the first user input is received when the first intravascular image is displayed as the live intravascular image and the intravascular imaging catheter is positioned within the first named segment during the movement;

modifying, in response to the first user input, the first named segment in the stylized diagram to have a different, second visual appearance such that the modification from the first visual appearance to the second visual appearance indicates that the intravascular imaging catheter is positioned within the first named segment during the movement.

20. An intravascular imaging system for use in peripheral vasculature, the system comprising:
an intravascular imaging catheter configured for intravascular ultrasound (IVUS) or optical coherence tomography (OCT);
a processor circuit configured for communication with the intravascular imaging catheter, wherein the processor circuit is configured to:
output, to a display in communication with the processor circuit, a screen display during live imaging by the intravascular imaging catheter, wherein the screen display comprises:
a live intravascular image obtained by the intravascular imaging catheter;
a stylized diagram of the peripheral vasculature, wherein the peripheral vasculature comprises a continuous length formed by a plurality of named segments, wherein the plurality of named segments comprises a common iliac vein (CIV) and an external iliac vein (EIV), wherein the CIV in the stylized diagram comprises a first visual appearance; and
a first instruction for a user to perform an action at a time when an event occurs, wherein the action comprises applying a CIV label, wherein the event comprises the live intravascular image depicting the CIV;
modify the live intravascular image to be a first plurality of intravascular images as the first plurality of intravascular images is obtained by the intravascular imaging catheter during movement of the intravascular imaging catheter through the EIV and the CIV;
receive, during the movement, a user input applying the CIV label to a first intravascular image of the first plurality of intravascular images, wherein the user input is received when the first intravascular image is displayed as the live intravascular image and the intravascular imaging catheter is positioned within the CIV during the movement;
modify, in response to the user input, the CIV in the stylized diagram to have a different, second visual appearance such that the modification from the first visual appearance to the second visual appearance indicates that the intravascular imaging catheter is positioned within the CIV during the movement.

* * * * *